(12) United States Patent
Kaspar et al.

(10) Patent No.: US 9,446,124 B2
(45) Date of Patent: Sep. 20, 2016

(54) TARGETING OF BONE MARROW NEOVASCULATURE

(71) Applicant: Philogen S.P.A., Siena (IT)

(72) Inventors: Manuela Kaspar, Brugg (CH); Christoph Schliemann, Munster (DE); Dario Neri, Buchs (CH)

(73) Assignee: Philochem AG, Zurich (CH)

( * ) Notice: Subject to any disclaimer, the term of this patent is extended or adjusted under 35 U.S.C. 154(b) by 26 days.

(21) Appl. No.: 14/219,145

(22) Filed: Mar. 19, 2014

(65) Prior Publication Data

US 2014/0199238 A1 Jul. 17, 2014

Related U.S. Application Data

(63) Continuation of application No. 13/386,451, filed as application No. PCT/EP2010/004727 on Aug. 2, 2010, now Pat. No. 8,679,488.

(60) Provisional application No. 61/231,564, filed on Aug. 5, 2009.

(51) Int. Cl.
| | |
|---|---|
| A61K 39/395 | (2006.01) |
| A61K 39/00 | (2006.01) |
| C07K 16/18 | (2006.01) |
| C07K 16/30 | (2006.01) |
| G01N 33/574 | (2006.01) |
| A61K 47/48 | (2006.01) |

(52) U.S. Cl.
CPC ..... *A61K 39/39558* (2013.01); *A61K 47/4863* (2013.01); *C07K 16/18* (2013.01); *C07K 16/3061* (2013.01); *G01N 33/57426* (2013.01); *C07K 2317/21* (2013.01); *C07K 2317/528* (2013.01); *C07K 2317/622* (2013.01); *C07K 2317/64* (2013.01)

(58) Field of Classification Search
None
See application file for complete search history.

(56) References Cited

U.S. PATENT DOCUMENTS

| | | | |
|---|---|---|---|
| 5,420,012 A | 5/1995 | Partanen et al. | |
| 5,571,679 A | 11/1996 | Sekiguchi et al. | |
| 7,968,685 B2 | 6/2011 | Brack et al. | |
| 2002/0187100 A1 | 12/2002 | Rizzieri et al. | |
| 2004/0185053 A1* | 9/2004 | Govindan ........ | A61K 47/48715 424/178.1 |
| 2006/0024757 A1 | 2/2006 | Hussa et al. | |
| 2006/0115428 A1 | 6/2006 | Menrad et al. | |
| 2006/0188501 A1 | 8/2006 | Homma et al. | |

FOREIGN PATENT DOCUMENTS

| | | |
|---|---|---|
| EP | 0 344 134 B1 | 11/1989 |
| EP | 0580859 | 2/1994 |
| EP | 0603735 | 6/1994 |
| WO | 01/83816 | 11/2001 |
| WO | 02/20563 | 3/2002 |
| WO | 2004/000216 | 12/2003 |
| WO | 2004/067038 | 8/2004 |
| WO | 2004/094612 | 11/2004 |
| WO | 2005/009366 | 2/2005 |
| WO | 2005/086612 | 9/2005 |
| WO | 2006/026020 | 3/2006 |
| WO | 2006/050834 | 5/2006 |
| WO | 2006/119897 | 11/2006 |
| WO | 2007/128563 | 11/2007 |
| WO | 2008/120101 | 10/2008 |
| WO | 2009/013619 | 1/2009 |
| WO | 2009/056268 | 5/2009 |
| WO | 2010/078945 | 7/2010 |
| WO | 2010/078950 | 7/2010 |

OTHER PUBLICATIONS

Villa et al., Int. J. Cancer: 2008, 122, 2405-2413.*
Padró et al., Blood, 2000, 95:2637-2644.*
Tijink, B.M., et al. "Radioimmunotherapy of head and neck cancer xenografts using 131I-labeled antibody L19-SIP for selective targeting of tumor vasculature." J Nucl Med. Jul. 2006;47(7):1127-35.
Viti, F., et al. "Increased binding affinity and valence of recombinant antibody fragments lead to improved targeting of tumoral angiogenesis." Cancer Res. Jan. 15, 1999;59(2):347-52.
Linnala, A., et al. "Isoforms of cellular fibronectin and tenascin in amniotic fluid." FEBS Lett. Jan. 10, 1994;337 (2):167-70.
Vartio, T., et al. "Differential expression of the ED sequence-containing form of cellular fibronectin in embryonic and adult human tissues." J Cell Sci. Nov. 1987;88 ( Pt 4):419-30.
Rybak, J.N., et al. "The extra-domain A of fibronectin is a vascular marker of solid tumors and metastases." Cancer Res. Nov. 15, 2007;67(22):10948-57.
Schwager, K., et al. "Preclinical characterization of DEKAVIL (F8-IL10), a novel clinical-stage immunocytokine which inhibits the progression of collagen-induced arthritis." Arthritis Res Ther. 2009;11(5):R142. Epub Sep. 25, 2009
Silacci, M., et al. "Human monoclonal antibodies to domain C of tenascin-C selectively target solid tumors in vivo." Protein Eng Des Sel. Oct. 2006;19(10):471-8. Epub Aug. 22, 2006.
Oyama, F., et al. "Oncodevelopmental regulation of the alternative splicing of fibronectin pre-messenger RNA in human lung tissues." Cancer Res. Feb. 15, 1990;50(4):1075-8.
Berndt, A., et al. "Evidence of ED-B+ fibronectin synthesis in human tissues by non-radioactive RNA in situ hybridization. Investigations on carcinoma (oral squamous cell and breast carcinoma), chronic inflammation (rheumatoid synovitis) and fibromatosis (Morbus Dupuytren)." Histochem Cell Biol. Mar. 1998;109(3):249-55.
Kriegsmann, J., et al. "Expression of fibronectin splice variants and oncofetal glycosylated fibronectin in the synovial membranes of patients with rheumatoid arthritis and osteoarthritis." Rheumatol Int. Jan. 2004;24(1):25-33. Epub Apr. 24, 2003.

(Continued)

*Primary Examiner* — Hong Sang
(74) *Attorney, Agent, or Firm* — Kathleen D. Rigaut; Patrick J. Hagan; Dann, Dorfman, Herrell and Skillman

(57) ABSTRACT

Antibodies which bind an antigen of the bone marrow neovasculature in leukemia patients, for use in treatment and diagnosis of leukemia, in particular the treatment and diagnosis of acute myeloid leukemia (AML).

7 Claims, 4 Drawing Sheets

(56) References Cited

OTHER PUBLICATIONS

Trachsel, E., et al. "Antibody-mediated delivery of IL-10 inhibits the progression of established collagen-induced arthritis." Arthritis Res Ther. 2007;9(1):R9.

Chevalier, X., et al. "Presence of ED-A containing fibronectin in human articular cartilage from patients with osteoarthritis and rheumatoid arthritis." J Rheumatol. Jun. 1996;23(6):1022-30.

Claudepierre, P., et al. "Increased Ed-B fibronectin plasma levels in spondyloarthropathies: comparison with rheumatoid arthritis patients and a healthy population." Rheumatology (Oxford). Nov. 1999;38(11):1099-103.

Davies, J., et al. "Affinity improvement of single antibody VH domains: residues in all three hypervariable regions affect antigen binding." Immunotechnology. Sep. 1996;2(3):169-79.

Liao, Y.F., et al. "The EIIIA segment of fibronectin is a ligand for integrins alpha 9beta 1 and alpha 4beta 1 providing a novel mechanism for regulating cell adhesion by alternative splicing." J Biol Chem. Apr. 26, 2002;277(17):14467-74. Epub Feb. 11, 2002.

Okamura, Y., et al. "The extra domain A of fibronectin activates Toll-like receptor 4." J Biol Chem. Mar. 30, 2001;276 (13):10229-33. Epub Jan. 9, 2001

Peters, J.H., et al. "Preferential recognition of a fragment species of osteoarthritic synovial fluid fibronectin by antibodies to the alternatively spliced Eiiia segment." Arthritis Rheum. Nov. 2001;44(11):2572-85.

Berndt, A., et al. "Differential expression of tenascin-C splicing domains in urothelial carcinomas of the urinary bladder." J Cancer Res Clin Oncol. Aug. 2006;132(8):537-46. Epub May 31, 2006.

Birchler, M., et al. "Selective targeting and photocoagulation of ocular angiogenesis mediated by a phage-derived human antibody fragment." Nat Biotechnol. Oct. 1999;17(10):984-8.

Paganelli, G., et al. "Pre-targeted immunodetection in glioma patients: tumour localization and single-photon emission tomography imaging of [99mTc]PnAO-biotin." Eur J Nucl Med. Apr. 1994;21(4):314-21.

Riva, P., et al. "Treatment of intracranial human glioblastoma by direct intratumoral administration of 131I-labelled anti-tenascin monoclonal antibody BC-2." Int J Cancer. Apr. 22, 1992;51(1):7-13.

Riva, P., et al. "Local treatment of malignant gliomas by direct infusion of specific monoclonal antibodies labeled with 131I: comparison of the results obtained in recurrent and newly diagnosed tumors." Cancer Res. Dec. 1, 1995;55(23 Suppl):5952s-5956s.

Schrama, D., et al. "Antibody targeted drugs as cancer therapeutics." Nat Rev Drug Discov. Feb. 2006;5(2):147-59.

Padro, T., et al. "Increased angiogenesis in the bone marrow of patients with acute myeloid leukemia." Blood. Apr. 15, 2000;95(8):2637-44.

Fabbrini, M., et al. "Selective occlusion of tumor blood vessels by targeted delivery of an antibody-photosensitizer conjugate." Int J Cancer. Apr. 1, 2006;118(7):1805-13.

Nilsson, F., et al. "Targeted delivery of tissue factor to the ED-B domain of fibronectin, a marker of angiogenesis, mediates the infarction of solid tumors in mice." Cancer Res. Jan. 15, 2001;61(2):711-6.

Marlind, J., et al. "Antibody-mediated delivery of interleukin-2 to the stroma of breast cancer strongly enhances the potency of chemotherapy." Clin Cancer Res. Oct. 15, 2008;14(20):6515-24.

Schliemann, C., et al. "Complete eradication of human B-cell lymphoma xenografts using rituximab in combination with the immunocytokine L19-IL2." Blood. Mar. 5, 2009;113(10):2275-83. Epub Nov. 12, 2008.

Wang, H.Y., et al. "Identification of a Mutated Fibronectin As a Tumor Antigen Recognized by CD4+ T Cells: Its Role in Extracellular Matrix Formation and Tumor Metastasis." Journal of Experimental Medicine. Jun. 3, 2002;195 (1):1397-1406.

Karp et al., "Targeting vascular endothelial growth factor for relapsed and refractory adult acute myelogenous leukemias: therapy with sequential 1-beta-d-arabinofuranosylcytosine, mitoxantrone, and bevacizumab." Clin. Cancer Res. Jun. 1, 2004; 10(11):3577-3585.

Padro et al., "Overexpression of vascular endothelial growth factor (VEGF) and its cellular receptor KDR (VEGFR-2) in the bone marrow of patients with acute myeloid leukemia." Leukemia, Jul. 16, 2002(7): 1302-1310.

Neri et al., "Interfering with pH regulation in tumours as a therapeutic strategy." Nat. Rev. Drug Discov., Sep. 16, 2011 (10)10: 767-777.

Beguin, Y., et al. "Soluble CD23 and other receptors (CD4, CD8, CD25, CD71) in serum of patients with chronic lymphocytic leukemia." Leukemia. Dec. 1993;7(12):2019-25.

Hussein, K., et al. "Opposite expression pattern of Src kinase Lyn in acute and chronic haematological malignancies." Ann Hematol. Nov. 2009;88(11):1059-67. Epub Mar. 17, 2009.

Rodig, S.J., et al. "Heterogeneous CD52 expression among hematologic neoplasms: implications for the use of alemtuzumab (CAMPATH-1H)." Clin Cancer Res. Dec. 1, 2006;12(23):7174-9.

Spaeth, N., et al. "Radioimmunotherapy targeting the extra domain B of fibronectin in C6 rat gliomas: a preliminary study about the therapeutic efficacy of iodine-131-labeled SIP(L19)." Nucl Med Biol. Jul. 2006;33(5):661-6.

Chilosi, M., et al. "Constitutive expression of tenascin in T-dependent zones of human lymphoid tissues." Am J Pathol. Nov. 1993;143(5):1348-55.

Holt, L.J., et al. "Domain antibodies: proteins for therapy." Trends Biotechnol. Nov. 2003;21(11):484-90.

Soini, Y., et al. "Tenascin immunoreactivity in normal and pathological bone marrow." J Clin Pathol. Mar. 1993;46 (3):218-21.

Estey, E.H. "Modulation of angiogenesis in patients with myelodysplastic syndrome." Best Pract Res Clin Haematol. Dec. 2004:17(4):623-39.

Smolej, L., et al. "Choice of endothelial marker is crucial for assessment of bone marrow microvessel density in chronic lymphocytic leukemia." APMIS. Dec. 2008;116(12):1058-62.

El-Sorady, M., et al. "Bone Marrow Angiogenesis in Patients with Hematological Malignancies: Role of VGF." Journal of the Egyptian Nat. Cancer Inst. Jun. 2000;12(2):131-132.

Aguayo, A., et al. "Angiogenesis in acute and chronic leukemias and myelodysplastic syndromes." Blood. Sep. 15, 2000;96(6):2240-5.

Schliemann, C., et al. "Three clinical-stage tumor targeting antibodies reveal differential expression of oncofetal fibronectin and tenascin-C isoforms in human lymphoma." Leuk Res. Dec. 2009; 33(12):1718-22. Epub Jul. 22, 2009.

Ballard, V.L., et al. "Vascular tenascin-C regulates cardiac endothelial phenotype and neovascularization." FASEB J. Apr. 2006;20(6):717-9. Epub Feb. 6, 2006.

Villa, A., et al. "A high-affinity human monoclonal antibody specific to the alternatively spliced EDA domain of fibronectin efficiently targets tumor neo-vasculature in vivo." Int J Cancer. Jun. 1, 2008;122(11):2405-13.

Castellani, P., et al. "Transformed human cells release different fibronectin variants than do normal cells." J Cell Biol. Nov. 1986;103(5):1671-7.

Borsi, L., et al. "Monoclonal antibodies in the analysis of fibronectin isoforms generated by alternative splicing of mRNA precursors in normal and transformed human cells." J Cell Biol. Mar. 1987;104(3):595-600.

Borsi, L., et al. "Expression of different tenascin isoforms in normal, hyperplastic and neoplastic human breast tissues." Int J Cancer. Nov. 11, 1992;52(5):688-92.

Zardi, L., et al. "Transformed human cells produce a new fibronectin isoform by preferential alternative splicing of a previously unobserved exon." Embo J. Aug. 1987;6(8):2337-42.

Carnemolla, B., et al. "Identification of a glioblastoma-associated tenascin-C isoform by a high affinity recombinant antibody." Am J Pathol. May 1999;154(5):1345-52.

Mariani, G.M., et al. "Tumor targeting potential of the monoclonal antibody BC-1 against oncofetal fibronectin in nude mice bearing human tumor implants." Cancer. Dec. 15, 1997;80(12 Suppl):2378-84.

(56) References Cited

OTHER PUBLICATIONS

Tarli, L., et al. "A high-affinity human antibody that targets tumoral blood vessels." Cancer. Dec. 15, 1987;80(12 Suppl):2378-84.

Carnemolla, B., et al. "A tumor-associated fibronectin isoform generated by alternative splicing of messenger RNA precursors." J Cell Biol. Mar. 1989;108(3):1139-48.

Carnemolla, B., et al. "Phage antibodies with pan-species recognition of the oncofoetal angiogenesis marker fibronectin ED-B domain." Int J Cancer. Nov. 4, 1996;68(3):397-405.

Castellani, P., et al. "The fibronectin isoform containing the ED-B oncofetal domain: a marker of angiogenesis." Int J Cancer. Dec. 1, 1994;59(5):612-8.

Oyama, F., et al. "Coordinate oncodevelopmental modulation of alternative splicing of fibronectin pre-messenger RNA at ED-A, ED-B, and CS1 regions in human liver tumors." Cancer Res. May 1, 1993;53(9):2005-11.

Balza, E., et al. "Transforming growth factor beta regulates the levels of different fibronectin isoforms in normal human cultured fibroblasts." FEBS Lett. Feb. 8, 1988;228(1):42-4.

Birchler, M., et al. "Infrared photodetection for the in vivo localisation of phage-derived antibodies directed against angiogenic markers." J Immunol Methods. Dec. 10, 1999;231(1-2):239-48.

Borsi, L., et al. "Transforming growth factor-beta regulates the splicing pattern of fibronectin messenger RNA precursor." FEBS Lett. Feb. 12, 1990;261(1):175-8.

Borsi, L. et al. "The alternative splicing pattern of the tenascin-C pre-mRNA is controlled by the extracellular pH." J Biol Chem. Mar. 17, 1995;270(11):6243-5.

Borsi, L., et al. "Preparation of phage antibodies to the ED-A domain of human fibronectin." Exp Cell Res. May 1, 1998;240(2):244-51.

Brack, S.S., et al. "Tumor-targeting properties of novel antibodies specific to the large isoform of tenascin-C." Clin Cancer Res. May 15, 2006;12(10):3200-8.

Giovannoni, L., et al. "Isolation of anti-angiogenesis antibodies from a large combinatorial repertoire by colony filter screening." Nucleic Acids Res. Mar. 1, 2001;29(5):E27.

Hanahan, D., et al. "The hallmarks of cancer." Cell. Jan. 7, 2000;100(1):57-70.

Kaspar, M., et al. "Fibronectin as target for tumor therapy." Int J Cancer. Mar. 15, 2006;118(6):1331-9.

Neri, D., et al. "Tumour vascular targeting." Nat Rev Cancer. Jun. 2005;5(6):436-46.

Oyama, F., et al. "Deregulation of alternative splicing of fibronectin pre-mRNA in malignant human liver tumors." J Biol Chem. Jun. 25, 1989;264(18):10331-4.

Rybak, J.N., et al. "Ligand-based vascular targeting of disease." ChemMedChem. Jan. 2007;2(1):22-40.

Scarpino, S., et al. "Expression of EDA/EDB isoforms of fibronectin in papillary carcinoma of the thyroid." J Pathol. Jun. 1999;188(2):163-7.

Thorpe, P.E. "Vascular targeting agents as cancer therapeutics." Clin Cancer Res. Jan. 15, 2004;10(2):415-27.

Trachsel, E., et al. "Antibodies for angiogenesis inhibition, vascular targeting and endothelial cell transcytosis." Adv Drug Deliv Rev. Aug. 7, 2006;58(5-6):735-54. Epub May 20, 2006.

Adams, G.P., et al. "High affinity restricts the localization and tumor penetration of single-chain fv antibody molecules." Cancer Res. Jun. 15, 2001;61(12):4750-5.

Berndorff, D., et al. "Imaging of tumor angiogenesis using 99mTc-labeled human recombinant anti-ED-B fibronectin antibody fragments." J Nucl Med. Oct. 2006;47(10):1707-16.

Berndorff, D., et al. "Radioimmunotherapy of solid tumors by targeting extra domain B fibronectin: identification of the best-suited radioimmunoconjugate." Clin Cancer Res. Oct. 1, 2005;11(19 Pt 2):7053s-7063s.

Borsi, L., et al. "Selective targeting of tumoral vasculature: comparison of different formats of an antibody (L19) to the ED-B domain of fibronectin." Int j Cancer. Nov. 1, 2002;102(1):75-85.

Burrows, F.J., et al. "Up-regulation of endoglin on vascular endothelial cells in human solid tumors: implications for diagnosis and therapy." Clin Cancer Res. Dec. 1995;1(12):1623-34.

Carnemolla, B., et al. "Enhancement of the antitumor properties of interleukin-2 by its targeted delivery to the tumor blood vessel extracellular matrix." Blood. Mar. 1, 2002;99(5):1659-65.

Castronovo, V., et al. "A chemical proteomics approach for the identification of accessible antigens expressed in human kidney cancer." Mol Cell Proteomics. Nov. 2006;5(11):2083-91. Epub Jul. 21, 2006

Demartis, S., et al. "Selective targeting of tumour neovasculature by a radiohalogenated human antibody fragment specific for the ED-B domain of fibronectin." Eur J Nucl Med. Apr. 2001;28(4):534-9.

Luster, T.A., et al. "Plasma protein beta-2-glycoprotein 1 mediates interaction between the anti-tumor monoclonal antibody 3G4 and anionic phospholipids on endothelial cells." J Biol Chem. Oct. 6, 2006;281(40):29863-71. Epub Aug. 10, 2006.

Menrad, A., et al. "ED-B fibronectin as a target for antibody-based cancer treatments." Expert Opin Ther Targets. Jun. 2005;9(3):491-500.

Niesner, U., et al. "Quantitation of the tumor-targeting properties of antibody fragments conjugated to cell-permeating HIV-1 TAT peptides." Bioconjug Chem. Jul.-Aug. 2002;13(4):729-36.

Payne, G., et al. "Progress in immunoconjugate cancer therapeutics." Cancer Cell. Mar. 2003;3(3):207-12.

Santimaria, M., et al. "Immunoscintigraphic detection of the ED-B domain of fibronectin, a marker of angiogenesis, in patients with cancer." Clin Cancer Res. Feb. 2003;9(2):571-9.

\* cited by examiner

A

B

A

B

SEQUENCE LISTING

```
<160> NUMBER OF SEQ ID NOS: 42

<210> SEQ ID NO 1
<211> LENGTH: 348
<212> TYPE: DNA
<213> ORGANISM: Homo sapiens

<400> SEQUENCE: 1
gaggtgcagc tgttggagtc tgggggaggc ttggtacagc ctgggggtc cctgagactc      60 tcctgtgcag cctctggatt cacctttagc cggtatggta tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtat attactgtgc gaaagcgcat    300
aatgcttttg actactgggg ccagggaacc ctggtcaccg tgtcgaga                 348

<210> SEQ ID NO 2
<211> LENGTH: 116
<212> TYPE: PRT
<213> ORGANISM: Homo sapiens

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala His Asn Ala Phe Asp Tyr Trp Gly Gln Gly Thr Leu Val
            100                 105                 110

Thr Val Ser Arg
        115

<210> SEQ ID NO 3
<211> LENGTH: 324
<212> TYPE: DNA
```

<213> ORGANISM: Homo sapiens

<400> SEQUENCE: 3

```
tcttctgagc tgactcagga ccctgctgtg tctgtggcct tgggacagac agtcaggatc      60
acatgccaag agacagcct  cagaagctat tatgcaagct ggtaccagca gaagccagga    120
caggcccctg tacttgtcat ctatggtaaa acaaccggc  cctcagggat cccagaccga    180
ttctctggct ccagctcagg aaacacagct tccttgacca tcactgggc  tcaggcggaa    240
gatgaggctg actattactg taactcctct gtttatacta tgccgcccgt ggtattcggc    300
ggagggacca agctgaccgt ccta                                           324
```

<210> SEQ ID NO 4
<211> LENGTH: 108
<212> TYPE: PRT
<213> ORGANISM: Homo sapiens

<400> SEQUENCE: 4

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ser Val Tyr Thr Met Pro Pro
                85                  90                  95

Val Val Phe Gly Gly Gly Thr Lys Leu Thr Val Leu
            100                 105

<210> SEQ ID NO 5
<211> LENGTH: 5
<212> TYPE: PRT
<213> ORGANISM: Homo sapiens

<400> SEQUENCE: 5

Arg Tyr Gly Met Ser
1               5

<210> SEQ ID NO 6
<211> LENGTH: 17
<212> TYPE: PRT
<213> ORGANISM: Homo sapiens

<400> SEQUENCE: 6

Ala Ile Ser Gly Ser Gly Gly Ser Thr Tyr Tyr Ala Asp Ser Val Lys
1               5                   10                  15

Gly

<210> SEQ ID NO 7
<211> LENGTH: 7
<212> TYPE: PRT
<213> ORGANISM: Homo sapiens

<400> SEQUENCE: 7

Ala His Asn Ala Phe Asp Tyr
1               5

<210> SEQ ID NO 8
<211> LENGTH: 11
<212> TYPE: PRT
<213> ORGANISM: Homo sapiens

<400> SEQUENCE: 8

Gln Gly Asp Ser Leu Arg Ser Tyr Tyr Ala Ser
1               5                   10

<210> SEQ ID NO 9
<211> LENGTH: 7
<212> TYPE: PRT
<213> ORGANISM: Homo sapiens

<400> SEQUENCE: 9

Gly Lys Asn Asn Arg Pro Ser
1               5

<210> SEQ ID NO 10
<211> LENGTH: 11
<212> TYPE: PRT
<213> ORGANISM: Homo sapiens

<400> SEQUENCE: 10

Asn Ser Ser Val Tyr Thr Met Pro Pro Val Val
1               5                   10

<210> SEQ ID NO 11
<211> LENGTH: 10
<212> TYPE: PRT
<213> ORGANISM: Artificial sequence
<220> FEATURE:
<223> OTHER INFORMATION: Synthetic sequence: 4A1-F16 VH and VL domain
      peptide linker amino acid sequence

<400> SEQUENCE: 11

Gly Gly Gly Ser Gly Gly Gly Ser Gly Gly
1               5                   10

<210> SEQ ID NO 12
<211> LENGTH: 275
<212> TYPE: DNA
<213> ORGANISM: Homo sapiens

<400> SEQUENCE: 12
gaggtgcagc tgttggagtc tgggggaggc ttggtacagc ctggggggtc cctgagactc      60
tcctgtgcag cctctggatt cacctttagc ctgtttacga tgagctgggt ccgccaggct     120
ccagggaagg ggctggagtg gtctcagct attagtggta gtggtggtag cacatactac      180
gcagactccg tgaagggccg gttcaccatc tccagagaca attccaagaa cacgctgtat     240
ctgcaaatga cagcctgag agccgaggac acggc                                 275

<210> SEQ ID NO 13
<211> LENGTH: 118
<212> TYPE: PRT
<213> ORGANISM: Homo sapiens

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Phe
            20                  25                  30

Thr Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
            115

<210> SEQ ID NO 14
<211> LENGTH: 324
<212> TYPE: DNA
<213> ORGANISM: Homo sapiens

<400> SEQUENCE: 14
gaaattgtgt tgacgcagtc tccaggcacc ctgtctttgt ctccagggga aagagccacc      60
ctctcctgca gggccagtca gagtgttagc atgccgtttt tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagatgcgtg gtcggccgcc gacgttcggc     300
caagggacca aggtggaaat caaa                                            324

<210> SEQ ID NO 15
<211> LENGTH: 108
<212> TYPE: PRT
<213> ORGANISM: Homo sapiens

<400> SEQUENCE: 15

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Met Pro
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys
            100                 105

<210> SEQ ID NO 16
<211> LENGTH: 3
<212> TYPE: PRT
<213> ORGANISM: Homo sapiens

<400> SEQUENCE: 16

Leu Phe Thr
1

<210> SEQ ID NO 17
<211> LENGTH: 6
<212> TYPE: PRT
<213> ORGANISM: Homo sapiens

<400> SEQUENCE: 17

Ser Gly Ser Gly Gly Ser
1               5

<210> SEQ ID NO 18
<211> LENGTH: 6
<212> TYPE: PRT
<213> ORGANISM: Homo sapiens

<400> SEQUENCE: 18

Ser Thr His Leu Tyr Leu
1               5

<210> SEQ ID NO 19
<211> LENGTH: 3
<212> TYPE: PRT
<213> ORGANISM: Homo sapiens

<400> SEQUENCE: 19

Met Pro Phe
1

<210> SEQ ID NO 20
<211> LENGTH: 7
<212> TYPE: PRT
<213> ORGANISM: Homo sapiens

<400> SEQUENCE: 20

Gly Ala Ser Ser Arg Ala Thr
1               5

<210> SEQ ID NO 21
<211> LENGTH: 6
<212> TYPE: PRT
<213> ORGANISM: Homo sapiens

<400> SEQUENCE: 21

Met Arg Gly Arg Pro Pro
1               5

<210> SEQ ID NO 22
<211> LENGTH: 14
<212> TYPE: PRT
<213> ORGANISM: Artificial sequence
<220> FEATURE:
<223> OTHER INFORMATION: Synthetic sequence: F8 (V5L/K18R) VH and VL
      domain peptide linker amino acid sequence

<400> SEQUENCE: 22

Gly Gly Gly Gly Ser Gly Gly Gly Ser Gly Gly Gly Gly Gly
1               5                   10

<210> SEQ ID NO 23
<211> LENGTH: 2
<212> TYPE: PRT
<213> ORGANISM: Artificial sequence
<220> FEATURE:
<223> OTHER INFORMATION: Synthetic sequence: 4A1-F16-SIP and F8-SIP
      (V5L/K18R) VL and CH4 domain peptide linker amino acid sequence

<400> SEQUENCE: 23

Ser Gly
1

<210> SEQ ID NO 24
<211> LENGTH: 119
<212> TYPE: PRT
<213> ORGANISM: Artificial sequence
<220> FEATURE:
<223> OTHER INFORMATION: Synthetic sequence: Amino acid sequence of CH4
      dimerization domain of 4A1-F16-SIP and F8-SIP (V5L/K18R)

<400> SEQUENCE: 24

Gly Ser Gly Gly Pro Arg Ala Ala Pro Glu Val Tyr Ala Phe Ala Thr
1               5                   10                  15

Pro Glu Trp Pro Gly Ser Arg Asp Lys Arg Thr Leu Ala Cys Leu Ile
            20                  25                  30

Gln Asn Phe Met Pro Glu Asp Ile Ser Val Gln Trp Leu His Asn Glu
        35                  40                  45

Val Gln Leu Pro Asp Ala Arg His Ser Thr Thr Gln Pro Arg Lys Thr
    50                  55                  60

Lys Gly Ser Gly Phe Phe Val Phe Ser Arg Leu Glu Val Thr Arg Ala
65                  70                  75                  80

Glu Trp Glu Gln Lys Asp Glu Phe Ile Cys Arg Ala Val His Glu Ala
                85                  90                  95

Ala Ser Pro Ser Gln Thr Val Gln Arg Ala Val Ser Val Asn Pro Glu
            100                 105                 110

Ser Ser Arg Arg Gly Gly Cys
        115

<210> SEQ ID NO 25
<211> LENGTH: 355
<212> TYPE: PRT
<213> ORGANISM: Artificial sequence
<220> FEATURE:
<223> OTHER INFORMATION: Synthetic sequence: 4A1-F16-SIP amino acid
      sequence

<400> SEQUENCE: 25

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala His Asn Ala Phe Asp Tyr Trp Gly Gln Gly Thr Leu Val
            100                 105                 110

Thr Val Ser Arg Gly Gly Gly Ser Gly Gly Ser Gly Gly Ser Ser
        115                 120                 125

Glu Leu Thr Gln Asp Pro Ala Val Ser Val Ala Leu Gly Gln Thr Val
    130                 135                 140

Arg Ile Thr Cys Gln Gly Asp Ser Leu Arg Ser Tyr Tyr Ala Ser Trp
145                 150                 155                 160

Tyr Gln Gln Lys Pro Gly Gln Ala Pro Val Leu Val Ile Tyr Gly Lys
                165                 170                 175

Asn Asn Arg Pro Ser Gly Ile Pro Asp Arg Phe Ser Gly Ser Ser Ser
            180                 185                 190

Gly Asn Thr Ala Ser Leu Thr Ile Thr Gly Ala Gln Ala Glu Asp Glu
        195                 200                 205

Ala Asp Tyr Tyr Cys Asn Ser Ser Val Tyr Thr Met Pro Pro Val Val
    210                 215                 220

Phe Gly Gly Gly Thr Lys Leu Thr Val Leu Ser Gly Ser Gly Gly
225                 230                 235                 240

Pro Arg Ala Ala Pro Glu Val Tyr Ala Phe Ala Thr Pro Glu Trp Pro
                245                 250                 255

Gly Ser Arg Asp Lys Arg Thr Leu Ala Cys Leu Ile Gln Asn Phe Met
            260                 265                 270

Pro Glu Asp Ile Ser Val Gln Trp Leu His Asn Glu Val Gln Leu Pro
        275                 280                 285

Asp Ala Arg His Ser Thr Thr Gln Pro Arg Lys Thr Lys Gly Ser Gly
    290                 295                 300

Phe Phe Val Phe Ser Arg Leu Glu Val Thr Arg Ala Glu Trp Glu Gln
305                 310                 315                 320

Lys Asp Glu Phe Ile Cys Arg Ala Val His Glu Ala Ala Ser Pro Ser
                325                 330                 335

Gln Thr Val Gln Arg Ala Val Ser Val Asn Pro Glu Ser Ser Arg Arg
            340                 345                 350

Gly Gly Cys
        355

<210> SEQ ID NO 26
<211> LENGTH: 361
<212> TYPE: PRT
<213> ORGANISM: Artificial sequence
<220> FEATURE:
<223> OTHER INFORMATION: Synthetic sequence: F8-SIP (V5L/K18R) amino
      acid sequence

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Phe
            20                  25                  30

Thr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser Gly Gly Gly Gly Ser Gly Gly Gly Ser Gly
        115                 120                 125

Gly Gly Gly Gly Glu Ile Val Leu Thr Gln Ser Pro Gly Thr Leu Ser
    130                 135                 140

Leu Ser Pro Gly Glu Arg Ala Thr Leu Ser Cys Arg Ala Ser Gln Ser

```
                145                 150                 155                 160
Val Ser Met Pro Phe Leu Ala Trp Tyr Gln Gln Lys Pro Gly Gln Ala
                    165                 170                 175

Pro Arg Leu Leu Ile Tyr Gly Ala Ser Ser Arg Ala Thr Gly Ile Pro
                180                 185                 190

Asp Arg Phe Ser Gly Ser Gly Ser Gly Thr Asp Phe Thr Leu Thr Ile
                195                 200                 205

Ser Arg Leu Glu Pro Glu Asp Phe Ala Val Tyr Tyr Cys Gln Gln Met
            210                 215                 220

Arg Gly Arg Pro Pro Thr Phe Gly Gln Gly Thr Lys Val Glu Ile Lys
225                 230                 235                 240

Ser Gly Gly Ser Gly Gly Pro Arg Ala Ala Pro Glu Val Tyr Ala Phe
                245                 250                 255

Ala Thr Pro Glu Trp Pro Gly Ser Arg Asp Lys Arg Thr Leu Ala Cys
                260                 265                 270

Leu Ile Gln Asn Phe Met Pro Glu Asp Ile Ser Val Gln Trp Leu His
                275                 280                 285

Asn Glu Val Gln Leu Pro Asp Ala Arg His Ser Thr Thr Gln Pro Arg
            290                 295                 300

Lys Thr Lys Gly Ser Gly Phe Phe Val Phe Ser Arg Leu Glu Val Thr
305                 310                 315                 320

Arg Ala Glu Trp Glu Gln Lys Asp Glu Phe Ile Cys Arg Ala Val His
                325                 330                 335

Glu Ala Ala Ser Pro Ser Gln Thr Val Gln Arg Ala Val Ser Val Asn
                340                 345                 350

Pro Glu Ser Ser Arg Arg Gly Gly Cys
                355                 360

<210> SEQ ID NO 27
<211> LENGTH: 153
<212> TYPE: PRT
<213> ORGANISM: Homo sapiens

<400> SEQUENCE: 27

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
        50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
                100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
        130                 135                 140

Cys Gln Ser Ile Ile Ser Thr Leu Thr
145                 150
```

```
<210> SEQ ID NO 28
<211> LENGTH: 14
<212> TYPE: PRT
<213> ORGANISM: Artificial sequence
<220> FEATURE:
<223> OTHER INFORMATION: Synthetic sequence: IL-2 linker sequence

<400> SEQUENCE: 28

Gly Gly Gly Gly Ser Gly Gly Gly Gly Ser Gly Gly Gly Gly
1               5                   10

<210> SEQ ID NO 29
<211> LENGTH: 15
<212> TYPE: PRT
<213> ORGANISM: Artificial sequence
<220> FEATURE:
<223> OTHER INFORMATION: Synthetic sequence: IL-2 linker sequence

<400> SEQUENCE: 29

Gly Gly Gly Gly Ser Gly Gly Gly Gly Ser Gly Gly Gly Gly Ser
1               5                   10                  15

<210> SEQ ID NO 30
<211> LENGTH: 15
<212> TYPE: PRT
<213> ORGANISM: Artificial sequence
<220> FEATURE:
<223> OTHER INFORMATION: Synthetic sequence: IL-2 linker sequence

<400> SEQUENCE: 30

Ser Ser Ser Ser Gly Ser Ser Ser Ser Gly Ser Ser Ser Ser Gly
1               5                   10                  15

<210> SEQ ID NO 31
<211> LENGTH: 15
<212> TYPE: PRT
<213> ORGANISM: Artificial sequence
<220> FEATURE:
<223> OTHER INFORMATION: Synthetic sequence: IL-2 linker sequence

<400> SEQUENCE: 31

Gly Ser Gly Ser Ala Gly Ser Gly Ser Ala Gly Ser Gly Ser Ala
1               5                   10                  15

<210> SEQ ID NO 32
<211> LENGTH: 15
<212> TYPE: PRT
<213> ORGANISM: Artificial sequence
<220> FEATURE:
<223> OTHER INFORMATION: Synthetic sequence: IL-2 linker sequence

<400> SEQUENCE: 32

Gly Gly Ser Gly Gly Gly Gly Ser Gly Gly Gly Gly Ser Gly Gly
1               5                   10                  15

<210> SEQ ID NO 33
<211> LENGTH: 5
<212> TYPE: PRT
<213> ORGANISM: Artificial sequence
<220> FEATURE:
<223> OTHER INFORMATION: Synthetic sequence: Linker motif

<400> SEQUENCE: 33

Gly Gly Gly Gly Ser
1               5
```

-continued

```
<210> SEQ ID NO 34
<211> LENGTH: 5
<212> TYPE: PRT
<213> ORGANISM: Artificial sequence
<220> FEATURE:
<223> OTHER INFORMATION: Synthetic sequence: Linker motif

<400> SEQUENCE: 34

Ser Ser Ser Ser Gly
1               5

<210> SEQ ID NO 35
<211> LENGTH: 5
<212> TYPE: PRT
<213> ORGANISM: Artificial sequence
<220> FEATURE:
<223> OTHER INFORMATION: Synthetic sequence: Linker motif

<400> SEQUENCE: 35

Gly Ser Gly Ser Ala
1               5

<210> SEQ ID NO 36
<211> LENGTH: 5
<212> TYPE: PRT
<213> ORGANISM: Artificial sequence
<220> FEATURE:
<223> OTHER INFORMATION: Synthetic sequence: Linker motif

<400> SEQUENCE: 36

Gly Gly Ser Gly Gly
1               5

<210> SEQ ID NO 37
<211> LENGTH: 2201
<212> TYPE: PRT
<213> ORGANISM: Homo sapiens

<400> SEQUENCE: 37

Met Gly Ala Met Thr Gln Leu Leu Ala Gly Val Phe Leu Ala Phe Leu
1               5                   10                  15

Ala Leu Ala Thr Glu Gly Gly Val Leu Lys Lys Val Ile Arg His Lys
                20                  25                  30

Arg Gln Ser Gly Val Asn Ala Thr Leu Pro Glu Glu Asn Gln Pro Val
            35                  40                  45

Val Phe Asn His Val Tyr Asn Ile Lys Leu Pro Val Gly Ser Gln Cys
        50                  55                  60

Ser Val Asp Leu Glu Ser Ala Ser Gly Glu Lys Asp Leu Ala Pro Pro
65                  70                  75                  80

Ser Glu Pro Ser Glu Ser Phe Gln Glu His Thr Val Asp Gly Glu Asn
                85                  90                  95

Gln Ile Val Phe Thr His Arg Ile Asn Ile Pro Arg Arg Ala Cys Gly
            100                 105                 110

Cys Ala Ala Ala Pro Asp Val Lys Glu Leu Leu Ser Arg Leu Glu Glu
        115                 120                 125

Leu Glu Asn Leu Val Ser Ser Leu Arg Glu Gln Cys Thr Ala Gly Ala
    130                 135                 140

Gly Cys Cys Leu Gln Pro Ala Thr Gly Arg Leu Asp Thr Arg Pro Phe
145                 150                 155                 160

Cys Ser Gly Arg Gly Asn Phe Ser Thr Glu Gly Cys Gly Cys Val Cys
                165                 170                 175
```

-continued

```
Glu Pro Gly Trp Lys Gly Pro Asn Cys Ser Glu Pro Glu Cys Pro Gly
                180                 185                 190

Asn Cys His Leu Arg Gly Arg Cys Ile Asp Gly Gln Cys Ile Cys Asp
            195                 200                 205

Asp Gly Phe Thr Gly Glu Asp Cys Ser Gln Leu Ala Cys Pro Ser Asp
        210                 215                 220

Cys Asn Asp Gln Gly Lys Cys Val Asn Gly Val Cys Ile Cys Phe Glu
225                 230                 235                 240

Gly Tyr Ala Gly Ala Asp Cys Ser Arg Glu Ile Cys Pro Val Pro Cys
                245                 250                 255

Ser Glu Glu His Gly Thr Cys Val Asp Gly Leu Cys Val Cys His Asp
            260                 265                 270

Gly Phe Ala Gly Asp Asp Cys Asn Lys Pro Leu Cys Leu Asn Asn Cys
        275                 280                 285

Tyr Asn Arg Gly Arg Cys Val Glu Asn Glu Cys Val Cys Asp Glu Gly
    290                 295                 300

Phe Thr Gly Glu Asp Cys Ser Glu Leu Ile Cys Pro Asn Asp Cys Phe
305                 310                 315                 320

Asp Arg Gly Arg Cys Ile Asn Gly Thr Cys Tyr Cys Glu Glu Gly Phe
                325                 330                 335

Thr Gly Glu Asp Cys Gly Lys Pro Thr Cys Pro His Ala Cys His Thr
            340                 345                 350

Gln Gly Arg Cys Glu Glu Gly Gln Cys Val Cys Asp Glu Gly Phe Ala
        355                 360                 365

Gly Leu Asp Cys Ser Glu Lys Arg Cys Pro Ala Asp Cys His Asn Arg
    370                 375                 380

Gly Arg Cys Val Asp Gly Arg Cys Glu Cys Asp Asp Gly Phe Thr Gly
385                 390                 395                 400

Ala Asp Cys Gly Glu Leu Lys Cys Pro Asn Gly Cys Ser His Gly
                405                 410                 415

Arg Cys Val Asn Gly Gln Cys Val Cys Asp Glu Gly Tyr Thr Gly Glu
            420                 425                 430

Asp Cys Ser Gln Leu Arg Cys Pro Asn Asp Cys His Ser Arg Gly Arg
        435                 440                 445

Cys Val Glu Gly Lys Cys Val Cys Glu Gln Gly Phe Lys Gly Tyr Asp
450                 455                 460

Cys Ser Asp Met Ser Cys Pro Asn Asp Cys His Gln His Gly Arg Cys
465                 470                 475                 480

Val Asn Gly Met Cys Val Cys Asp Asp Gly Tyr Thr Gly Glu Asp Cys
                485                 490                 495

Arg Asp Arg Gln Cys Pro Arg Asp Cys Ser Asn Arg Gly Leu Cys Val
            500                 505                 510

Asp Gly Gln Cys Val Cys Glu Asp Gly Phe Thr Gly Pro Asp Cys Ala
        515                 520                 525

Glu Leu Ser Cys Pro Asn Asp Cys His Gly Gln Gly Arg Cys Val Asn
    530                 535                 540

Gly Gln Cys Val Cys His Glu Gly Phe Met Gly Lys Asp Cys Lys Glu
545                 550                 555                 560

Gln Arg Cys Pro Ser Asp Cys His Gly Gln Gly Arg Cys Val Asp Gly
                565                 570                 575

Gln Cys Ile Cys His Glu Gly Phe Thr Gly Leu Asp Cys Gly Gln His
            580                 585                 590

Ser Cys Pro Ser Asp Cys Asn Asn Leu Gly Gln Cys Val Ser Gly Arg
```

-continued

```
              595                 600                 605
Cys Ile Cys Asn Glu Gly Tyr Ser Gly Glu Asp Cys Ser Glu Val Ser
        610                 615                 620

Pro Pro Lys Asp Leu Val Val Thr Glu Val Thr Glu Thr Val Asn
625                 630                 635                 640

Leu Ala Trp Asp Asn Glu Met Arg Val Thr Glu Tyr Leu Val Tyr
                645                 650                 655

Thr Pro Thr His Glu Gly Gly Leu Glu Met Gln Phe Arg Val Pro Gly
                660                 665                 670

Asp Gln Thr Ser Thr Ile Ile Gln Glu Leu Glu Pro Gly Val Glu Tyr
            675                 680                 685

Phe Ile Arg Val Phe Ala Ile Leu Glu Asn Lys Lys Ser Ile Pro Val
            690                 695                 700

Ser Ala Arg Val Ala Thr Tyr Leu Pro Ala Pro Glu Gly Leu Lys Phe
705                 710                 715                 720

Lys Ser Ile Lys Glu Thr Ser Val Glu Val Glu Trp Asp Pro Leu Asp
                725                 730                 735

Ile Ala Phe Glu Thr Trp Glu Ile Ile Phe Arg Asn Met Asn Lys Glu
                740                 745                 750

Asp Glu Gly Glu Ile Thr Lys Ser Leu Arg Arg Pro Glu Thr Ser Tyr
            755                 760                 765

Arg Gln Thr Gly Leu Ala Pro Gly Gln Glu Tyr Glu Ile Ser Leu His
    770                 775                 780

Ile Val Lys Asn Asn Thr Arg Gly Pro Gly Leu Lys Arg Val Thr Thr
785                 790                 795                 800

Thr Arg Leu Asp Ala Pro Ser Gln Ile Glu Val Lys Asp Val Thr Asp
                805                 810                 815

Thr Thr Ala Leu Ile Thr Trp Phe Lys Pro Leu Ala Glu Ile Asp Gly
            820                 825                 830

Ile Glu Leu Thr Tyr Gly Ile Lys Asp Val Pro Gly Asp Arg Thr Thr
        835                 840                 845

Ile Asp Leu Thr Glu Asp Glu Asn Gln Tyr Ser Ile Gly Asn Leu Lys
    850                 855                 860

Pro Asp Thr Glu Tyr Glu Val Ser Leu Ile Ser Arg Arg Gly Asp Met
865                 870                 875                 880

Ser Ser Asn Pro Ala Lys Glu Thr Phe Thr Thr Gly Leu Asp Ala Pro
            885                 890                 895

Arg Asn Leu Arg Arg Val Ser Gln Thr Asp Asn Ser Ile Thr Leu Glu
        900                 905                 910

Trp Arg Asn Gly Lys Ala Ala Ile Asp Ser Tyr Arg Ile Lys Tyr Ala
    915                 920                 925

Pro Ile Ser Gly Gly Asp His Ala Glu Val Asp Val Pro Lys Ser Gln
930                 935                 940

Gln Ala Thr Thr Lys Thr Thr Leu Thr Gly Leu Arg Pro Gly Thr Glu
945                 950                 955                 960

Tyr Gly Ile Gly Val Ser Ala Val Lys Glu Asp Lys Glu Ser Asn Pro
                965                 970                 975

Ala Thr Ile Asn Ala Ala Thr Glu Leu Asp Thr Pro Lys Asp Leu Gln
            980                 985                 990

Val Ser Glu Thr Ala Glu Thr Ser  Leu Thr Leu Leu Trp Lys Thr Pro
        995                 1000                1005

Leu Ala Lys Phe Asp Arg Tyr  Arg Leu Asn Tyr Ser  Leu Pro Thr
    1010                1015                1020
```

```
Gly Gln Trp Val Gly Val Gln Leu Pro Arg Asn Thr Thr Ser Tyr
1025                1030                1035

Val Leu Arg Gly Leu Glu Pro Gly Gln Glu Tyr Asn Val Leu Leu
1040                1045                1050

Thr Ala Glu Lys Gly Arg His Lys Ser Lys Pro Ala Arg Val Lys
1055                1060                1065

Ala Ser Thr Glu Gln Ala Pro Glu Leu Glu Asn Leu Thr Val Thr
1070                1075                1080

Glu Val Gly Trp Asp Gly Leu Arg Leu Asn Trp Thr Ala Ala Asp
1085                1090                1095

Gln Ala Tyr Glu His Phe Ile Ile Gln Val Gln Glu Ala Asn Lys
1100                1105                1110

Val Glu Ala Ala Arg Asn Leu Thr Val Pro Gly Ser Leu Arg Ala
1115                1120                1125

Val Asp Ile Pro Gly Leu Lys Ala Ala Thr Pro Tyr Thr Val Ser
1130                1135                1140

Ile Tyr Gly Val Ile Gln Gly Tyr Arg Thr Pro Val Leu Ser Ala
1145                1150                1155

Glu Ala Ser Thr Gly Glu Thr Pro Asn Leu Gly Glu Val Val Val
1160                1165                1170

Ala Glu Val Gly Trp Asp Ala Leu Lys Leu Asn Trp Thr Ala Pro
1175                1180                1185

Glu Gly Ala Tyr Glu Tyr Phe Phe Ile Gln Val Gln Glu Ala Asp
1190                1195                1200

Thr Val Glu Ala Ala Gln Asn Leu Thr Val Pro Gly Gly Leu Arg
1205                1210                1215

Ser Thr Asp Leu Pro Gly Leu Lys Ala Ala Thr His Tyr Thr Ile
1220                1225                1230

Thr Ile Arg Gly Val Thr Gln Asp Phe Ser Thr Thr Pro Leu Ser
1235                1240                1245

Val Glu Val Leu Thr Glu Glu Val Pro Asp Met Gly Asn Leu Thr
1250                1255                1260

Val Thr Glu Val Ser Trp Asp Ala Leu Arg Leu Asn Trp Thr Thr
1265                1270                1275

Pro Asp Gly Thr Tyr Asp Gln Phe Thr Ile Gln Val Gln Glu Ala
1280                1285                1290

Asp Gln Val Glu Glu Ala His Asn Leu Thr Val Pro Gly Ser Leu
1295                1300                1305

Arg Ser Met Glu Ile Pro Gly Leu Arg Ala Gly Thr Pro Tyr Thr
1310                1315                1320

Val Thr Leu His Gly Glu Val Arg Gly His Ser Thr Arg Pro Leu
1325                1330                1335

Ala Val Glu Val Val Thr Glu Asp Leu Pro Gln Leu Gly Asp Leu
1340                1345                1350

Ala Val Ser Glu Val Gly Trp Asp Gly Leu Arg Leu Asn Trp Thr
1355                1360                1365

Ala Ala Asp Asn Ala Tyr Glu His Phe Val Ile Gln Val Gln Glu
1370                1375                1380

Val Asn Lys Val Glu Ala Ala Gln Asn Leu Thr Leu Pro Gly Ser
1385                1390                1395

Leu Arg Ala Val Asp Ile Pro Gly Leu Glu Ala Ala Thr Pro Tyr
1400                1405                1410
```

-continued

```
Arg Val Ser Ile Tyr Gly Val Ile Arg Gly Tyr Arg Thr Pro Val
    1415                1420                1425

Leu Ser Ala Glu Ala Ser Thr Ala Lys Glu Pro Glu Ile Gly Asn
    1430                1435                1440

Leu Asn Val Ser Asp Ile Thr Pro Glu Ser Phe Asn Leu Ser Trp
    1445                1450                1455

Met Ala Thr Asp Gly Ile Phe Glu Thr Phe Thr Ile Glu Ile Ile
    1460                1465                1470

Asp Ser Asn Arg Leu Leu Glu Thr Val Glu Tyr Asn Ile Ser Gly
    1475                1480                1485

Ala Glu Arg Thr Ala His Ile Ser Gly Leu Pro Pro Ser Thr Asp
    1490                1495                1500

Phe Ile Val Tyr Leu Ser Gly Leu Ala Pro Ser Ile Arg Thr Lys
    1505                1510                1515

Thr Ile Ser Ala Thr Ala Thr Thr Glu Ala Leu Pro Leu Leu Glu
    1520                1525                1530

Asn Leu Thr Ile Ser Asp Ile Asn Pro Tyr Gly Phe Thr Val Ser
    1535                1540                1545

Trp Met Ala Ser Glu Asn Ala Phe Asp Ser Phe Leu Val Thr Val
    1550                1555                1560

Val Asp Ser Gly Lys Leu Leu Asp Pro Gln Glu Phe Thr Leu Ser
    1565                1570                1575

Gly Thr Gln Arg Lys Leu Glu Leu Arg Gly Leu Ile Thr Gly Ile
    1580                1585                1590

Gly Tyr Glu Val Met Val Ser Gly Phe Thr Gln Gly His Gln Thr
    1595                1600                1605

Lys Pro Leu Arg Ala Glu Ile Val Thr Glu Ala Glu Pro Glu Val
    1610                1615                1620

Asp Asn Leu Leu Val Ser Asp Ala Thr Pro Asp Gly Phe Arg Leu
    1625                1630                1635

Ser Trp Thr Ala Asp Glu Gly Val Phe Asp Asn Phe Val Leu Lys
    1640                1645                1650

Ile Arg Asp Thr Lys Lys Gln Ser Glu Pro Leu Glu Ile Thr Leu
    1655                1660                1665

Leu Ala Pro Glu Arg Thr Arg Asp Leu Thr Gly Leu Arg Glu Ala
    1670                1675                1680

Thr Glu Tyr Glu Ile Glu Leu Tyr Gly Ile Ser Lys Gly Arg Arg
    1685                1690                1695

Ser Gln Thr Val Ser Ala Ile Ala Thr Thr Ala Met Gly Ser Pro
    1700                1705                1710

Lys Glu Val Ile Phe Ser Asp Ile Thr Glu Asn Ser Ala Thr Val
    1715                1720                1725

Ser Trp Arg Ala Pro Thr Ala Gln Val Glu Ser Phe Arg Ile Thr
    1730                1735                1740

Tyr Val Pro Ile Thr Gly Gly Thr Pro Ser Met Val Thr Val Asp
    1745                1750                1755

Gly Thr Lys Thr Gln Thr Arg Leu Val Lys Leu Ile Pro Gly Val
    1760                1765                1770

Glu Tyr Leu Val Ser Ile Ile Ala Met Lys Gly Phe Glu Glu Ser
    1775                1780                1785

Glu Pro Val Ser Gly Ser Phe Thr Thr Ala Leu Asp Gly Pro Ser
    1790                1795                1800

Gly Leu Val Thr Ala Asn Ile Thr Asp Ser Glu Ala Leu Ala Arg
```

-continued

```
            1805                1810                1815

Trp Gln Pro Ala Ile Ala Thr Val Asp Ser Tyr Val Ile Ser Tyr
        1820                1825                1830

Thr Gly Glu Lys Val Pro Glu Ile Thr Arg Thr Val Ser Gly Asn
        1835                1840                1845

Thr Val Glu Tyr Ala Leu Thr Asp Leu Glu Pro Ala Thr Glu Tyr
        1850                1855                1860

Thr Leu Arg Ile Phe Ala Glu Lys Gly Pro Gln Lys Ser Ser Thr
        1865                1870                1875

Ile Thr Ala Lys Phe Thr Thr Asp Leu Asp Ser Pro Arg Asp Leu
        1880                1885                1890

Thr Ala Thr Glu Val Gln Ser Glu Thr Ala Leu Leu Thr Trp Arg
        1895                1900                1905

Pro Pro Arg Ala Ser Val Thr Gly Tyr Leu Leu Val Tyr Glu Ser
        1910                1915                1920

Val Asp Gly Thr Val Lys Glu Val Ile Val Gly Pro Asp Thr Thr
        1925                1930                1935

Ser Tyr Ser Leu Ala Asp Leu Ser Pro Ser Thr His Tyr Thr Ala
        1940                1945                1950

Lys Ile Gln Ala Leu Asn Gly Pro Leu Arg Ser Asn Met Ile Gln
        1955                1960                1965

Thr Ile Phe Thr Thr Ile Gly Leu Leu Tyr Pro Phe Pro Lys Asp
        1970                1975                1980

Cys Ser Gln Ala Met Leu Asn Gly Asp Thr Thr Ser Gly Leu Tyr
        1985                1990                1995

Thr Ile Tyr Leu Asn Gly Asp Lys Ala Gln Ala Leu Glu Val Phe
        2000                2005                2010

Cys Asp Met Thr Ser Asp Gly Gly Gly Trp Ile Val Phe Leu Arg
        2015                2020                2025

Arg Lys Asn Gly Arg Glu Asn Phe Tyr Gln Asn Trp Lys Ala Tyr
        2030                2035                2040

Ala Ala Gly Phe Gly Asp Arg Arg Glu Glu Phe Trp Leu Gly Leu
        2045                2050                2055

Asp Asn Leu Asn Lys Ile Thr Ala Gln Gly Gln Tyr Glu Leu Arg
        2060                2065                2070

Val Asp Leu Arg Asp His Gly Glu Thr Ala Phe Ala Val Tyr Asp
        2075                2080                2085

Lys Phe Ser Val Gly Asp Ala Lys Thr Arg Tyr Lys Leu Lys Val
        2090                2095                2100

Glu Gly Tyr Ser Gly Thr Ala Gly Asp Ser Met Ala Tyr His Asn
        2105                2110                2115

Gly Arg Ser Phe Ser Thr Phe Asp Lys Asp Thr Asp Ser Ala Ile
        2120                2125                2130

Thr Asn Cys Ala Leu Ser Tyr Lys Gly Ala Phe Trp Tyr Arg Asn
        2135                2140                2145

Cys His Arg Val Asn Leu Met Gly Arg Tyr Gly Asp Asn Asn His
        2150                2155                2160

Ser Gln Gly Val Asn Trp Phe His Trp Lys Gly His Glu His Ser
        2165                2170                2175

Ile Gln Phe Ala Glu Met Lys Leu Arg Pro Ser Asn Phe Arg Asn
        2180                2185                2190

Leu Glu Gly Arg Arg Lys Arg Ala
        2195                2200
```

<210> SEQ ID NO 38
<211> LENGTH: 7560
<212> TYPE: DNA
<213> ORGANISM: Homo sapiens

<400> SEQUENCE: 38

```
accggccaca gcctgcctac tgtcacccgc ctctcccgcg cgcagataca cgcccccgcc      60
tccgtgggca caaaggcagc gctgctgggg aactcggggg aacgcgcacg tgggaaccgc     120
cgcagctcca cactccaggt acttcttcca aggacctagg tctctcgccc atcggaaaga     180
aaataattct ttcaagaaga tcagggacaa ctgatttgaa gtctactctg tgcttctaaa     240
tccccaattc tgctgaaagt gaatccctag agccctagag ccccagcagc acccagccaa     300
acccacctcc accatggggg ccatgactca gctgttggca ggtgtctttc ttgctttcct     360
tgccctcgct accgaaggtg gggtcctcaa gaaagtcatc cggcacaagc gacagagtgg     420
ggtgaacgcc accctgccag aagagaacca gccagtggtg tttaaccacg tttacaacat     480
caagctgcca gtgggatccc agtgttcggt ggatctggag tcagccagtg gggagaaaga     540
cctggcaccg ccttcagagc ccagcgaaag ctttcaggag cacacagtag atggggaaaa     600
ccagattgtc ttcacacatc gcatcaacat cccccgccgg gcctgtggct gtgccgcagc     660
ccctgatgtt aaggagctgc tgagcagact ggaggagctg gagaacctgg tgtcttccct     720
gagggagcaa tgtactgcag gagcaggctg ctgtctccag cctgccacag gccgcttgga     780
caccaggccc ttctgtagcg gtcggggcaa cttcagcact gaaggatgtg gctgtgtctg     840
cgaacctggc tggaaaggcc ccaactgctc tgagcccgaa tgtccaggca actgtcacct     900
tcgaggccgg tgcattgatg ggcagtgcat ctgtgacgac ggcttcacgg gcgaggactg     960
cagccagctg gcttgcccca cgactgcaa tgaccagggc aagtgcgtga atggagtctg    1020
catctgtttc gaaggctacg ccggggctga ctgcagccgt gaaatctgcc cagtgccctg    1080
cagtgaggag cacggcacat gtgtagatgg cttgtgtgtg tgccacgatg gctttgcagg    1140
cgatgactgc aacaagcctc tgtgtctcaa caattgctac aaccgtggac gatgcgtgga    1200
gaatgagtgc gtgtgtgatg agggtttcac gggcgaagac tgcagtgagc tcatctgccc    1260
caatgactgc ttcgaccggg gccgctgcat caatggcacc tgctactgcg aagaaggctt    1320
cacaggtgaa gactgcggga acccaccctg cccacatgcc tgccacaccc agggccggtg    1380
tgaggagggg cagtgtgtat gtgatgaggg cttttccggt ttggactgca gcgagaagag    1440
gtgtcctgct gactgtcaca atcgtggccg ctgtgtagac gggcggtgtg agtgtgatga    1500
tggtttcact ggagctgact gtggggagct caagtgtccc aatggctgca gtggccatgg    1560
ccgctgtgtc aatgggcagt gtgtgtgtga tgagggctat actggggagg actgcagcca    1620
gctacggtgc cccaatgact gtcacagtcg gggccgctgt gtcgagggca atgtgtatg    1680
tgagcaaggc ttcaagggct atgactgcag tgacatgagc tgccctaatg actgtcacca    1740
gcacggccgc tgtgtgaatg catgtgtgt ttgtgatgac ggctacacag gggaagactg    1800
ccggatcgc caatgcccca gggactgcag caacagggc ctctgtgtgg acggacagtg    1860
cgtctgtgag gacggcttca ccggccctga ctgtgcagaa ctctcctgtc caatgactg    1920
ccatggccag gtcgctgtg tgaatgggca gtgcgtgtgc catgaaggat ttatgggcaa    1980
agactgcaag gagcaaagat gtcccagtga ctgtcatggc cagggccgct gcgtggacgg    2040
ccagtgcatc tgccacgagg gcttcacagg cctggactgt ggccagcact cctgccccag    2100
```

-continued

```
tgactgcaac aacttaggac aatgcgtctc gggccgctgc atctgcaacg agggctacag   2160
cggagaagac tgctcagagg tgtctcctcc caaagacctc gttgtgacag aagtgacgga   2220
agagacggtc aacctggcct gggacaatga gatgcgggtc acagagtacc ttgtcgtgta   2280
cacgcccacc cacgagggtg gtctggaaat gcagttccgt gtgcctgggg accagacgtc   2340
caccatcatc caggagctgg agcctggtgt ggagtacttt atccgtgtat ttgccatcct   2400
ggagaacaag aagagcattc ctgtcagcgc cagggtggcc acgtacttac ctgcacctga   2460
aggcctgaaa ttcaagtcca tcaaggagac atctgtggaa gtggagtggg atcctctaga   2520
cattgctttt gaaacctggg agatcatctt ccggaatatg aataaagaag atgagggaga   2580
gatcaccaaa agcctgagga ggccagagac ctcttaccgg caaactggtc tagctcctgg   2640
gcaagagtat gagatatctc tgcacatagt gaaaaacaat acccgggccc ctggcctgaa   2700
gagggtgacc accacacgct ggatgccccc cagccagatc gaggtgaaag atgtcacaga   2760
caccactgcc ttgatcacct ggttcaagcc cctggctgag atcgatggca ttgagctgac   2820
ctacggcatc aaagacgtgc caggagaccg taccaccatc gatctcacag aggacgagaa   2880
ccagtactcc atcgggaacc tgaagcctga cactgagtac gaggtgtccc tcatctcccg   2940
cagaggtgac atgtcaagca acccagccaa agagaccttc acaacaggcc tcgatgctcc   3000
caggaatctt cgacgtgttt cccagacaga taacagcatc ccctggaat ggaggaatgg   3060
caaggcagct attgacagtt acagaattaa gtatgccccc atctctggag gggaccacgc   3120
tgaggttgat gttccaaaga gccaacaagc cacaaccaaa accacactca caggtctgag   3180
gccgggaact gaatatggga ttggagtttc tgctgtgaag aagacaaggc agagcaatcc   3240
agcgaccatc aacgcagcca cagagttgga cacgcccaag gaccttcagg tttctgaaac   3300
tgcagagacc agcctgaccc tgctctggaa gacaccgttg gccaaatttg accgctaccg   3360
cctcaattac agtctcccca caggccagtg ggtgggagtg cagcttccaa gaaacaccac   3420
ttcctatgtc ctgagaggcc tggaaccagg acaggagtac aatgtcctcc tgacagccga   3480
gaaaggcaga cacaagagca agcccgcacg tgtgaaggca tccactgaac aagcccctga   3540
gctggaaaac ctcaccgtga ctgaggttgg ctgggatggc ctcagactca actgaccgc   3600
ggctgaccag gcctatgagc actttatcat tcaggtgcag gaggccaaca aggtggaggc   3660
agctcggaac ctcaccgtgc ctggcagcct tcgggctgtg acataccgg gcctcaaggc   3720
tgctacgcct tatacagtct ccatctatgg ggtgatccag ggctatagaa caccagtgct   3780
ctctgctgag gcctccacag gggaaactcc caatttggga gaggtcgtgg tggccgaggt   3840
gggctgggat gccctcaaac tcaactggac tgctccagaa ggggcctatg agtactttt   3900
cattcaggtg caggaggctg acacagtaga ggcagcccag aacctcaccg tcccaggagg   3960
actgaggtcc acagacctgc ctgggctcaa agcagccact cattatacca tcaccatccg   4020
cggggtcact caggacttca gcacaacccc tctctctgtt gaagtcttga cagaggaggt   4080
tccagatatg ggaaacctca cagtgaccga ggttagctgg gatgctctca gactgaactg   4140
gaccacgcca gatggaacct atgaccagtt tactattcag gtccaggagg ctgaccaggt   4200
ggaagaggct cacaatctca cggttcctgg cagcctgcgt tccatggaaa tcccaggcct   4260
cagggctggc actccttaca cagtcacccc tgcacggcga g tcaggggcc acagcactcg   4320
accccttgct gtagaggtcg tcacagagga tctcccacag ctgggagatt tagccgtgtc   4380
tgaggttggc tgggatggcc tcagactcaa ctggaccgca gctgacaatg cctatgagca   4440
cttgtcatt caggtgcagg aggtcaacaa agtggaggca gcccagaacc tcacgttgcc   4500
```

```
tggcagcctc agggctgtgg acatcccggg cctcgaggct gccacgcctt atagagtctc    4560
catctatggg gtgatccggg gctatagaac accagtactc tctgctgagg cctccacagc    4620
caaagaacct gaaattggaa acttaaatgt ttctgacata actcccgaga gcttcaatct    4680
ctcctggatg gctaccgatg ggatcttcga gacctttacc attgaaatta ttgattccaa    4740
taggttgctg gagactgtgg aatataatat ctctggtgct gaacgaactg cccatatctc    4800
agggctaccc cctagtactg attttattgt ctacctctct ggacttgctc ccagcatccg    4860
gaccaaaacc atcagtgcca cagccacgac agaggccctg ccccttctgg aaaacctaac    4920
catttccgac attaatccct acgggttcac agtttcctgg atggcatcgg agaatgcctt    4980
tgacagcttt ctagtaacgg tggtggattc tgggaagctg ctggaccccc aggaattcac    5040
actttcagga acccagagga agctggagct tagaggcctc ataactggca ttggctatga    5100
ggttatggtc tctggcttca cccaagggca tcaaaccaag cccttgaggg ctgagattgt    5160
tacagaagcc gaaccggaag ttgacaacct tctggtttca gatgccaccc cagacggttt    5220
ccgtctgtcc tggacagctg atgaagggt cttcgacaat tttgttctca aaatcagaga    5280
taccaaaaag cagtctgagc cactggaaat aaccctactt gcccccgaac gtaccaggga    5340
cttaacaggt ctcagagagg ctactgaata cgaaattgaa ctctatggaa taagcaaagg    5400
aaggcgatcc cagacagtca gtgctatagc aacaacagcc atgggctccc caaggaagt    5460 cattttctca gacatcactg aaaattcggc tactgtcagc tggagggcac ccacggccca    5520
agtggagagc ttccggatta cctatgtgcc cattacagga ggtacaccct ccatggtaac    5580
tgtggacgga accaagactc agaccaggct ggtgaaactc atacctggcg tggagtacct    5640
tgtcagcatc atcgccatga agggctttga ggaaagtgaa cctgtctcag ggtcattcac    5700
cacagctctg gatggcccat ctggcctggt gacagccaac atcactgact cagaagcctt    5760
ggccaggtgg cagccagcca ttgccactgt ggacagttat gtcatctcct acacaggcga    5820
gaaagtgcca gaaattacac gcacggtgtc cgggaacaca gtggagtatg ctctgaccga    5880
cctcgagcct gccacggaat acacactgag aatcttttgca gagaaagggc cccagaagag    5940
ctcaaccatc actgccaagt tcacaacaga cctcgattct ccaagagact tgactgctac    6000
tgaggttcag tcggaaactg ccctccttac ctggcgaccc cccgggcat cagtcaccgg    6060 ttacctgctg gtctatgaat cagtggatgg cacagtcaag gaagtcattg tgggtccaga    6120
taccacctcc tacagcctgg cagacctgag cccatccacc cactacacag ccaagatcca    6180
ggcactcaat gggcccctga ggagcaatat gatccagacc atcttcacca caattggact    6240
cctgtacccc ttccccaagg actgctccca agcaatgctg aatggagaca cgacctctgg    6300
cctctacacc atttatctga atggtgataa ggctcaggcg ctggaagtct tctgtgacat    6360
gacctctgat gggggtggat ggattgtgtt cctgagacgc aaaaacggac gcgagaactt    6420
ctaccaaaac tggaaggcat atgctgctgg attggggac cgcagagaag aattctggct    6480
tgggctggac aacctgaaca aaatcacagc ccaggggcag tacgagctcc gggtggacct    6540
gcgggaccat ggggagacag cctttgctgt ctatgacaag ttcagcgtgg gagatgccaa    6600
gactcgctac aagctgaagg tggaggggta cagtgggaca gcaggtgact ccatggccta    6660
ccacaatggc agatccttct ccacctttga caaggacaca gattcagcca tcaccaactg    6720
tgctctgtcc tacaaagggg cttttctggta caggaactgt caccgtgtca acctgatggg    6780
gagatatggg gacaataacc acagtcaggg cgttaactgg ttccactgga agggccacga    6840
```

```
acactcaatc cagtttgctg agatgaagct gagaccaagc aacttcagaa atcttgaagg    6900
caggcgcaaa cgggcataaa ttggagggac cactgggtga gagaggaata aggcggccca    6960
gagcgaggaa aggattttac caaagcatca atacaaccag cccaaccatc ggtccacacc    7020
tgggcatttg gtgagaatca aagctgacca tggatccctg gggccaacgg caacagcatg    7080
ggcctcacct cctctgtgat ttctttcttt gcaccaaaga catcagtctc caacatgttt    7140
ctgttttgtt gtttgattca gcaaaaatct cccagtgaca acatcgcaat agttttttac    7200
ttctcttagg tggctctggg atgggagagg ggtaggatgt acaggggtag tttgtttttag   7260 aaccagccgt attttacatg aagctgtata attaattgtc attattttg ttagcaaaga    7320 ttaaatgtgt cattggaagc atcccttttt tttacatttc atacaacaga aaccagaaaa    7380
gcaatactgt ttccatttta aggatatgat taatattatt aatataataa tgatgatgat    7440
gatgatgaaa actaaggatt tttcaagaga tctttctttc caaaacattt ctggacagta    7500
cctgattgta ttttttttt aaataaaagc acaagtactt ttgaaaaaaa accggaattc    7560
```

<210> SEQ ID NO 39
<211> LENGTH: 90
<212> TYPE: PRT
<213> ORGANISM: Homo sapiens

<400> SEQUENCE: 39

Asn Ile Asp Arg Pro Lys Gly Leu Ala Phe Thr Asp Val Asp Val
1               5                   10                  15

Ser Ile Lys Ile Ala Trp Glu Ser Pro Gln Gly Gln Val Ser Arg Tyr
            20                  25                  30

Arg Val Thr Tyr Ser Ser Pro Glu Asp Gly Ile His Glu Leu Phe Pro
        35                  40                  45

Ala Pro Asp Gly Glu Glu Asp Thr Ala Glu Leu Gln Gly Leu Arg Pro
    50                  55                  60

Gly Ser Glu Tyr Thr Val Ser Val Val Ala Leu His Asp Asp Met Glu
65                  70                  75                  80

Ser Gln Pro Leu Ile Gly Thr Gln Ser Thr
                85                  90

<210> SEQ ID NO 40
<211> LENGTH: 2201
<212> TYPE: PRT
<213> ORGANISM: Homo sapiens

<400> SEQUENCE: 40

Met Gly Ala Met Thr Gln Leu Leu Ala Gly Val Phe Leu Ala Phe Leu
1               5                   10                  15

Ala Leu Ala Thr Glu Gly Gly Val Leu Lys Lys Val Ile Arg His Lys
            20                  25                  30

Arg Gln Ser Gly Val Asn Ala Thr Leu Pro Glu Glu Asn Gln Pro Val
        35                  40                  45

Val Phe Asn His Val Tyr Asn Ile Lys Leu Pro Val Gly Ser Gln Cys
    50                  55                  60

Ser Val Asp Leu Glu Ser Ala Ser Gly Glu Lys Asp Leu Ala Pro Pro
65                  70                  75                  80

Ser Glu Pro Ser Glu Ser Phe Gln Glu His Thr Val Asp Gly Glu Asn
                85                  90                  95

Gln Ile Val Phe Thr His Arg Ile Asn Ile Pro Arg Arg Ala Cys Gly
            100                 105                 110

-continued

Cys Ala Ala Ala Pro Asp Val Lys Glu Leu Leu Ser Arg Leu Glu Glu
            115                 120                 125

Leu Glu Asn Leu Val Ser Ser Leu Arg Glu Gln Cys Thr Ala Gly Ala
        130                 135                 140

Gly Cys Cys Leu Gln Pro Ala Thr Gly Arg Leu Asp Thr Arg Pro Phe
145                 150                 155                 160

Cys Ser Gly Arg Gly Asn Phe Ser Thr Glu Gly Cys Gly Cys Val Cys
                165                 170                 175

Glu Pro Gly Trp Lys Gly Pro Asn Cys Ser Glu Pro Glu Cys Pro Gly
            180                 185                 190

Asn Cys His Leu Arg Gly Arg Cys Ile Asp Gly Gln Cys Ile Cys Asp
        195                 200                 205

Asp Gly Phe Thr Gly Glu Asp Cys Ser Gln Leu Ala Cys Pro Ser Asp
    210                 215                 220

Cys Asn Asp Gln Gly Lys Cys Val Asn Gly Val Cys Ile Cys Phe Glu
225                 230                 235                 240

Gly Tyr Ala Gly Ala Asp Cys Ser Arg Glu Ile Cys Pro Val Pro Cys
                245                 250                 255

Ser Glu Glu His Gly Thr Cys Val Asp Gly Leu Cys Val Cys His Asp
            260                 265                 270

Gly Phe Ala Gly Asp Asp Cys Asn Lys Pro Leu Cys Leu Asn Asn Cys
        275                 280                 285

Tyr Asn Arg Gly Arg Cys Val Glu Asn Glu Cys Val Cys Asp Glu Gly
    290                 295                 300

Phe Thr Gly Glu Asp Cys Ser Glu Leu Ile Cys Pro Asn Asp Cys Phe
305                 310                 315                 320

Asp Arg Gly Arg Cys Ile Asn Gly Thr Cys Tyr Cys Glu Glu Gly Phe
                325                 330                 335

Thr Gly Glu Asp Cys Gly Lys Pro Thr Cys Pro His Ala Cys His Thr
            340                 345                 350

Gln Gly Arg Cys Glu Glu Gly Gln Cys Val Cys Asp Glu Gly Phe Ala
        355                 360                 365

Gly Val Asp Cys Ser Glu Lys Arg Cys Pro Ala Asp Cys His Asn Arg
370                 375                 380

Gly Arg Cys Val Asp Gly Arg Cys Glu Cys Asp Asp Gly Phe Thr Gly
385                 390                 395                 400

Ala Asp Cys Gly Glu Leu Lys Cys Pro Asn Gly Cys Ser Gly His Gly
                405                 410                 415

Arg Cys Val Asn Gly Gln Cys Val Cys Asp Glu Gly Tyr Thr Gly Glu
            420                 425                 430

Asp Cys Ser Gln Leu Arg Cys Pro Asn Asp Cys His Ser Arg Gly Arg
        435                 440                 445

Cys Val Glu Gly Lys Cys Val Cys Glu Gln Gly Phe Lys Gly Tyr Asp
450                 455                 460

Cys Ser Asp Met Ser Cys Pro Asn Asp Cys His Gln His Gly Arg Cys
465                 470                 475                 480

Val Asn Gly Met Cys Val Cys Asp Asp Gly Tyr Thr Gly Glu Asp Cys
                485                 490                 495

Arg Asp Arg Gln Cys Pro Arg Asp Cys Ser Asn Arg Gly Leu Cys Val
            500                 505                 510

Asp Gly Gln Cys Val Cys Glu Asp Gly Phe Thr Gly Pro Asp Cys Ala
        515                 520                 525

Glu Leu Ser Cys Pro Asn Asp Cys His Gly Gln Gly Arg Cys Val Asn

```
              530                 535                 540
Gly Gln Cys Val Cys His Glu Gly Phe Met Gly Lys Asp Cys Lys Glu
545                 550                 555                 560

Gln Arg Cys Pro Ser Asp Cys His Gly Gln Gly Arg Cys Val Asp Gly
                565                 570                 575

Gln Cys Ile Cys His Glu Gly Phe Thr Gly Leu Asp Cys Gly Gln His
            580                 585                 590

Ser Cys Pro Ser Asp Cys Asn Asn Leu Gly Gln Cys Val Ser Gly Arg
        595                 600                 605

Cys Ile Cys Asn Glu Gly Tyr Ser Gly Glu Asp Cys Ser Glu Val Ser
    610                 615                 620

Pro Pro Lys Asp Leu Val Val Thr Glu Val Thr Glu Glu Thr Val Asn
625                 630                 635                 640

Leu Ala Trp Asp Asn Glu Met Arg Val Thr Glu Tyr Leu Val Val Tyr
                645                 650                 655

Thr Pro Thr His Glu Gly Gly Leu Glu Met Gln Phe Arg Val Pro Gly
            660                 665                 670

Asp Gln Thr Ser Thr Ile Ile Gln Glu Leu Glu Pro Gly Val Glu Tyr
        675                 680                 685

Phe Ile Arg Val Phe Ala Ile Leu Glu Asn Lys Lys Ser Ile Pro Val
    690                 695                 700

Ser Ala Arg Val Ala Thr Tyr Leu Pro Ala Pro Glu Gly Leu Lys Phe
705                 710                 715                 720

Lys Ser Ile Lys Glu Thr Ser Val Glu Val Glu Trp Asp Pro Leu Asp
                725                 730                 735

Ile Ala Phe Glu Thr Trp Glu Ile Ile Phe Arg Asn Met Asn Lys Glu
            740                 745                 750

Asp Glu Gly Glu Ile Thr Lys Ser Leu Arg Arg Pro Gly Thr Ser Tyr
        755                 760                 765

Arg Gln Thr Gly Leu Ala Pro Gly Gln Glu Tyr Glu Ile Ser Leu His
    770                 775                 780

Ile Val Lys Asn Asn Thr Arg Gly Pro Gly Leu Lys Arg Val Thr Thr
785                 790                 795                 800

Thr Arg Leu Asp Ala Pro Ser Gln Ile Glu Val Lys Asp Val Thr Asp
                805                 810                 815

Thr Thr Ala Leu Ile Thr Trp Phe Lys Pro Leu Ala Glu Ile Asp Gly
            820                 825                 830

Ile Glu Leu Thr Tyr Gly Ile Lys Asp Val Pro Gly Asp Arg Thr Thr
        835                 840                 845

Ile Asp Leu Thr Glu Asp Glu Asn Gln Tyr Ser Ile Gly Asn Leu Lys
    850                 855                 860

Pro Asp Thr Glu Tyr Glu Val Ser Leu Ile Ser Arg Arg Gly Asp Met
865                 870                 875                 880

Ser Ser Asn Pro Ala Lys Glu Thr Phe Thr Thr Gly Leu Asp Ala Pro
                885                 890                 895

Arg Asn Leu Arg Arg Val Ser Gln Thr Asp Asn Ser Ile Thr Leu Glu
            900                 905                 910

Trp Arg Asn Gly Lys Ala Ala Ile Asp Ser Tyr Arg Ile Lys Tyr Ala
        915                 920                 925

Pro Ile Ser Gly Gly Asp His Ala Glu Val Asp Val Pro Lys Ser Gln
    930                 935                 940

Gln Ala Thr Thr Lys Thr Thr Leu Thr Gly Leu Arg Pro Gly Thr Glu
945                 950                 955                 960
```

-continued

Tyr Gly Ile Gly Val Ser Ala Val Lys Glu Asp Lys Glu Ser Asn Pro
              965                 970                 975

Ala Thr Ile Asn Ala Ala Thr Glu Leu Asp Thr Pro Lys Asp Leu Gln
              980                 985                 990

Val Ser Glu Thr Ala Glu Thr Ser Leu Thr Leu Leu Trp Lys Thr Pro
              995                 1000                1005

Leu Ala Lys Phe Asp Arg Tyr Arg Leu Asn Tyr Ser Leu Pro Thr
         1010                1015                1020

Gly Gln Trp Val Gly Val Gln Leu Pro Arg Asn Thr Thr Ser Tyr
         1025                1030                1035

Val Leu Arg Gly Leu Glu Pro Gly Gln Glu Tyr Asn Val Leu Leu
         1040                1045                1050

Thr Ala Glu Lys Gly Arg His Lys Ser Lys Pro Ala Arg Val Lys
         1055                1060                1065

Ala Ser Thr Glu Gln Ala Pro Glu Leu Glu Asn Leu Thr Val Thr
         1070                1075                1080

Glu Val Gly Trp Asp Gly Leu Arg Leu Asn Trp Thr Ala Ala Asp
         1085                1090                1095

Gln Ala Tyr Glu His Phe Ile Ile Gln Val Gln Glu Ala Asn Lys
         1100                1105                1110

Val Glu Ala Ala Arg Asn Leu Thr Val Pro Gly Ser Leu Arg Ala
         1115                1120                1125

Val Asp Ile Pro Gly Leu Lys Ala Ala Thr Pro Tyr Thr Val Ser
         1130                1135                1140

Ile Tyr Gly Val Ile Gln Gly Tyr Arg Thr Pro Val Leu Ser Ala
         1145                1150                1155

Glu Ala Ser Thr Gly Glu Thr Pro Asn Leu Gly Glu Val Val Val
         1160                1165                1170

Ala Glu Val Gly Trp Asp Ala Leu Lys Leu Asn Trp Thr Ala Pro
         1175                1180                1185

Glu Gly Ala Tyr Glu Tyr Phe Phe Ile Gln Val Gln Glu Ala Asp
         1190                1195                1200

Thr Val Glu Ala Ala Gln Asn Leu Thr Val Pro Gly Gly Leu Arg
         1205                1210                1215

Ser Thr Asp Leu Pro Gly Leu Lys Ala Ala Thr His Tyr Thr Ile
         1220                1225                1230

Thr Ile Arg Gly Val Thr Gln Asp Phe Ser Thr Thr Pro Leu Ser
         1235                1240                1245

Val Glu Val Leu Thr Glu Glu Val Pro Asp Met Gly Asn Leu Thr
         1250                1255                1260

Val Thr Glu Val Ser Trp Asp Ala Leu Arg Leu Asn Trp Thr Thr
         1265                1270                1275

Pro Asp Gly Thr Tyr Asp Gln Phe Thr Ile Gln Val Gln Glu Ala
         1280                1285                1290

Asp Gln Val Glu Glu Ala His Asn Leu Thr Val Pro Gly Ser Leu
         1295                1300                1305

Arg Ser Met Glu Ile Pro Gly Leu Arg Ala Gly Thr Pro Tyr Thr
         1310                1315                1320

Val Thr Leu His Gly Glu Val Arg Gly His Ser Thr Arg Pro Leu
         1325                1330                1335

Ala Val Glu Val Val Thr Glu Asp Leu Pro Gln Leu Gly Asp Leu
         1340                1345                1350

```
Ala Val Ser Glu Val Gly Trp Asp Gly Leu Arg Leu Asn Trp Thr
1355                1360                1365

Ala Ala Asp Asn Ala Tyr Glu His Phe Val Ile Gln Val Gln Glu
1370                1375                1380

Val Asn Lys Val Glu Ala Ala Gln Asn Leu Thr Leu Pro Gly Ser
1385                1390                1395

Leu Arg Ala Val Asp Ile Pro Gly Leu Glu Ala Ala Thr Pro Tyr
1400                1405                1410

Arg Val Ser Ile Tyr Gly Val Ile Arg Gly Tyr Arg Thr Pro Val
1415                1420                1425

Leu Ser Ala Glu Ala Ser Thr Ala Lys Glu Pro Glu Ile Gly Asn
1430                1435                1440

Leu Asn Val Ser Asp Ile Thr Pro Glu Ser Phe Asn Leu Ser Trp
1445                1450                1455

Met Ala Thr Asp Gly Ile Phe Glu Thr Phe Thr Ile Glu Ile Ile
1460                1465                1470

Asp Ser Asn Arg Leu Leu Glu Thr Val Glu Tyr Asn Ile Ser Gly
1475                1480                1485

Ala Glu Arg Thr Ala His Ile Ser Gly Leu Pro Pro Ser Thr Asp
1490                1495                1500

Phe Ile Val Tyr Leu Ser Gly Leu Ala Pro Ser Ile Arg Thr Lys
1505                1510                1515

Thr Ile Ser Ala Thr Ala Thr Thr Glu Ala Leu Pro Leu Leu Glu
1520                1525                1530

Asn Leu Thr Ile Ser Asp Ile Asn Pro Tyr Gly Phe Thr Val Ser
1535                1540                1545

Trp Met Ala Ser Glu Asn Ala Phe Asp Ser Phe Leu Val Thr Val
1550                1555                1560

Val Asp Ser Gly Lys Leu Leu Asp Pro Gln Glu Phe Thr Leu Ser
1565                1570                1575

Gly Thr Gln Arg Lys Leu Glu Leu Arg Gly Leu Ile Thr Gly Ile
1580                1585                1590

Gly Tyr Glu Val Met Val Ser Gly Phe Thr Gln Gly His Gln Thr
1595                1600                1605

Lys Pro Leu Arg Ala Glu Ile Val Thr Glu Ala Glu Pro Glu Val
1610                1615                1620

Asp Asn Leu Leu Val Ser Asp Ala Thr Pro Asp Gly Phe Arg Leu
1625                1630                1635

Ser Trp Thr Ala Asp Glu Gly Val Phe Asp Asn Phe Val Leu Lys
1640                1645                1650

Ile Arg Asp Thr Lys Lys Gln Ser Glu Pro Leu Glu Ile Thr Leu
1655                1660                1665

Leu Ala Pro Glu Arg Thr Arg Asp Ile Thr Gly Leu Arg Glu Ala
1670                1675                1680

Thr Glu Tyr Glu Ile Glu Leu Tyr Gly Ile Ser Lys Gly Arg Arg
1685                1690                1695

Ser Gln Thr Val Ser Ala Ile Ala Thr Thr Ala Met Gly Ser Pro
1700                1705                1710

Lys Glu Val Ile Phe Ser Asp Ile Thr Glu Asn Ser Ala Thr Val
1715                1720                1725

Ser Trp Arg Ala Pro Thr Ala Gln Val Glu Ser Phe Arg Ile Thr
1730                1735                1740

Tyr Val Pro Ile Thr Gly Gly Thr Pro Ser Met Val Thr Val Asp
```

-continued

```
            1745                1750                1755
Gly Thr Lys Thr Gln Thr Arg Leu Val Lys Leu Ile Pro Gly Val
        1760                1765                1770
Glu Tyr Leu Val Ser Ile Ile Ala Met Lys Gly Phe Glu Glu Ser
        1775                1780                1785
Glu Pro Val Ser Gly Ser Phe Thr Thr Ala Leu Asp Gly Pro Ser
        1790                1795                1800
Gly Leu Val Thr Ala Asn Ile Thr Asp Ser Glu Ala Leu Ala Arg
        1805                1810                1815
Trp Gln Pro Ala Ile Ala Thr Val Asp Ser Tyr Val Ile Ser Tyr
        1820                1825                1830
Thr Gly Glu Lys Val Pro Glu Ile Thr Arg Thr Val Ser Gly Asn
        1835                1840                1845
Thr Val Glu Tyr Ala Leu Thr Asp Leu Glu Pro Ala Thr Glu Tyr
        1850                1855                1860
Thr Leu Arg Ile Phe Ala Glu Lys Gly Pro Gln Lys Ser Ser Thr
        1865                1870                1875
Ile Thr Ala Lys Phe Thr Thr Asp Leu Asp Ser Pro Arg Asp Leu
        1880                1885                1890
Thr Ala Thr Glu Val Gln Ser Glu Thr Ala Leu Leu Thr Trp Arg
        1895                1900                1905
Pro Pro Arg Ala Ser Val Thr Gly Tyr Leu Leu Val Tyr Glu Ser
        1910                1915                1920
Val Asp Gly Thr Val Lys Glu Val Ile Val Gly Pro Asp Thr Thr
        1925                1930                1935
Ser Tyr Ser Leu Ala Asp Leu Ser Pro Ser Thr His Tyr Thr Ala
        1940                1945                1950
Lys Ile Gln Ala Leu Asn Gly Pro Leu Arg Ser Asn Met Ile Gln
        1955                1960                1965
Thr Ile Phe Thr Thr Ile Gly Leu Leu Tyr Pro Phe Pro Lys Asp
        1970                1975                1980
Cys Ser Gln Ala Met Leu Asn Gly Asp Thr Thr Ser Gly Leu Tyr
        1985                1990                1995
Thr Ile Tyr Leu Asn Gly Asp Lys Ala Glu Ala Leu Glu Val Phe
        2000                2005                2010
Cys Asp Met Thr Ser Asp Gly Gly Gly Trp Ile Val Phe Leu Arg
        2015                2020                2025
Arg Lys Asn Gly Arg Glu Asn Phe Tyr Gln Asn Trp Lys Ala Tyr
        2030                2035                2040
Ala Ala Gly Phe Gly Asp Arg Arg Glu Glu Phe Trp Leu Gly Leu
        2045                2050                2055
Asp Asn Leu Asn Lys Ile Thr Ala Gln Gly Gln Tyr Glu Leu Arg
        2060                2065                2070
Val Asp Leu Arg Asp His Gly Glu Thr Ala Phe Ala Val Tyr Asp
        2075                2080                2085
Lys Phe Ser Val Gly Asp Ala Lys Thr Arg Tyr Lys Leu Lys Val
        2090                2095                2100
Glu Gly Tyr Ser Gly Thr Ala Gly Asp Ser Met Ala Tyr His Asn
        2105                2110                2115
Gly Arg Ser Phe Ser Thr Phe Asp Lys Asp Thr Asp Ser Ala Ile
        2120                2125                2130
Thr Asn Cys Ala Leu Ser Tyr Lys Gly Ala Phe Trp Tyr Arg Asn
        2135                2140                2145
```

```
Cys His Arg Val Asn Leu Met Gly Arg Tyr Gly Asp Asn Asn His
    2150            2155            2160

Ser Gln Gly Val Asn Trp Phe His Trp Lys Gly His Glu His Ser
    2165            2170            2175

Ile Gln Phe Ala Glu Met Lys Leu Arg Pro Ser Asn Phe Arg Asn
    2180            2185            2190

Leu Glu Gly Arg Arg Lys Arg Ala
    2195            2200

<210> SEQ ID NO 41
<211> LENGTH: 91
<212> TYPE: PRT
<213> ORGANISM: Homo sapiens

<400> SEQUENCE: 41

Glu Gln Ala Pro Glu Leu Glu Asn Leu Thr Val Thr Glu Val Gly Trp
1               5                   10                  15

Asp Gly Leu Arg Leu Asn Trp Thr Ala Ala Asp Gln Ala Tyr Glu His
            20                  25                  30

Phe Ile Ile Gln Val Gln Glu Ala Asn Lys Val Glu Ala Ala Arg Asn
        35                  40                  45

Leu Thr Val Pro Gly Ser Leu Arg Ala Val Asp Ile Pro Gly Leu Lys
    50                  55                  60

Ala Ala Thr Pro Tyr Thr Val Ser Ile Tyr Gly Val Ile Gln Gly Tyr
65                  70                  75                  80

Arg Thr Pro Val Leu Ser Ala Glu Ala Ser Thr
                85                  90

<210> SEQ ID NO 42
<211> LENGTH: 273
<212> TYPE: DNA
<213> ORGANISM: Homo sapiens

<400> SEQUENCE: 42
gaacaagccc ctgagctgga aaacctcacc gtgactgagg ttggctggga tggcctcaga    60
ctcaactgga ccgcagctga ccaggcctat gagcacttta tcattcaggt gcaggaggcc   120
aacaaggtgg aggcagctcg gaacctcacc gtgcctggca gccttcgggc tgtggacata   180
ccgggcctca aggctgctac gccttataca gtctccatct atgggtgat ccagggctat    240 agaacaccag tgctctctgc tgaggcctcc aca                                273
```

TARGETING OF BONE MARROW NEOVASCULATURE

The present application is continuation of U.S. patent application Ser. No. 13/386,451 filed Jan. 23, 2012, now U.S. Pat. No. 8,679,488 which is §371 application of PCT/EP2010/004727 filed Aug. 2, 2010 which claims priority to U.S. Provisional Patent Application No. 61/231,564, filed Aug. 5, 2009, the entire disclosure of each being incorporated by reference herein.

The present invention relates to the use of antibodies which target an antigen expressed in bone marrow neovasculature, in particular the use of such antibodies for treating or diagnosing leukaemia.

Bone marrow neovascular structures are a characteristic feature of a number of diseases, including leukaemias, myelodysplastic syndromes (also sometimes referred to as preleukaemias) and multiple myeloma.

Leukaemia is a cancer of the blood and bone marrow which is characterized by an abnormal proliferation of blood cells. Blood cells are produced in the bone marrow where they develop from stem cells. The first stage in the development of blood cells is the differentiation of stem cells into myeloid stem cells or lymphoid stem cells. In healthy individuals, the myeloid stem cells then continue to differentiate into one of three types of mature blood cells: red blood cells, white blood cells and platelets, while the lymphoid stem cells differentiate into another type of white blood cells, referred to as lymphocytes. Either of these two cell lineages can be affected by leukaemia. Depending on the cell lineage affected, the leukaemias is referred to either as a myeloid (or alternatively as myelocytic, myelogenous, myeloblastic or non-lymphocytic) leukaemia, or a lymphocytic (or alternatively as lymphoblastic or lymphogenous) leukaemia.

In addition, leukaemias are also differentiated on the basis of whether the disease is acute or chronic. As the name implies, acute leukaemias progress rapidly while chronic leukaemia progress slowly and develop over many years. In acute forms of the disease, the affected bone marrow releases large numbers of immature white blood cells, called blasts or blast cells, which cannot carry out the normal white blood cell functions. If left untreated, acute leukaemias lead to death within a matter of weeks.

The most common form of acute leukaemia in adults, and the second most common leukaemia in children, is acute myeloid leukaemia (AML). AML, as the name implies, affects the myeloid rather than lymphocytic white blood cells and is therefore also sometimes referred to as non-lymphocytic leukaemia (ANLL).

Leukaemias differ from most other cancers in that the do not normally form static tumours. Rare exceptions include solid tumours composed of blast cells occurring outside the bone marrow in AML patients. These tumours are referred to as extramedullary myeloid tumours (or alternatively as chloroma, granulocytic sarcoma or myeloid sarcoma) and the disease is then called extramedullary AML.

Acute forms of leukaemia are usually treated using chemotherapy. For example, common treatment regimens for AML include cytarabine administered either alone or, more commonly, in combination with an anthracycline such as daunorubicin or idarubicin. However, despite the availability of aggressive multi-agent chemotherapy regimens, only 20-30% of AML patients are currently cured. The reason for this low success rate is the emergence of dominant, multi-drug and radiation resistant subclones of leukaemia cells. The insidious nature of AML also relates to the fact that, while all circulating blasts in the blood and most blasts in readily accessible bone marrow regions are rapidly killed by cytarabine-based chemotherapeutic regimens, some blasts in bone marrow sanctuaries survive chemotherapy and grow again at the end of treatment, causing a relapse. Any treatments which would allow these resistant blasts to be eradicated, preferably without causing major additional toxicity to the bone marrow, would represent a major advance in the treatment of leukaemia.

The present inventors have discovered that certain antigens are expressed in bone marrow neovasculature, such as the neovasculature found in the bone marrow of leukaemia patients.

Specifically, the present inventors have shown that tenascin-C, and the Extra Domain-A (ED-A) isoform of fibronectin, are expressed in neovascular structures present in bone marrow biopsies obtained from AML patients.

That an increase in angiogenesis takes place in the bone marrow of patients with AML has been previously reported (Padro et al., 2000). However, it was not known that antigens exist which are specifically expressed in the neovascular structures in the bone marrow these patients.

The discovery of these antigens opens up new avenues for treating and diagnosing diseases characterized by the presence of bone marrow neovasculature, including all those mentioned herein, such as leukaemia, myelodysplastic syndromes, and multiple myeloma.

For example, conventional chemotherapeutic treatments for leukaemia do not discriminate between diseased and healthy tissues. Consequently, large drug doses have to be administered to the patient to reach therapeutically relevant concentrations, leading to side effects such as toxicities to healthy tissues. In contrast, antibodies which bind the bone marrow neovasculature in leukaemia patients allow therapeutic agents to be delivered directly to the affected tissues, thus avoiding or reducing the disadvantages associated with conventional chemotherapeutic treatments. In addition, favourable toxicity profiles of site-specific therapeutics may also open new avenues in the therapy of diseases characterized by the presence of bone marrow neovasculature by allowing the systemic administration of highly potent and promising agents, which are currently either given at suboptimal doses or whose clinical application has to date been impeded by unacceptable toxicities when applied in an unmodified form.

Thus an aspect of the invention provides an antibody for use in a method of treatment of a disease characterised by bone marrow neovasculature, such as leukaemia, myelodysplastic syndromes, or multiple myeloma, wherein the antibody binds an antigen of the bone marrow neovasculature in patients suffering from said disease.

Another aspect of the present invention provides use of an antibody that binds an antigen of the bone marrow neovasculature in patients suffering from a disease characterized by bone marrow neovasculature, such as leukaemia, myelodysplastic syndromes, or multiple myeloma, in the manufacture of a medicament for use in a method of treating said disease.

Another aspect of the present invention provides a method of treating a disease characterized by bone marrow neovasculature, comprising administering a therapeutically effective amount of an antibody that binds an antigen of the bone marrow neovasculature in patients suffering from said disease to an individual in need thereof.

Another aspect of the present invention provides an antibody that binds an antigen of the bone marrow neovasculature in patients suffering from a disease characterised by bone marrow neovasculature, such as leukaemia, myelodysplastic syndromes, or multiple myeloma, for use in a method of treating said disease, the method comprising administering the antibody and an anti-cancer compound to an individual in need thereof.

Another aspect of the present invention provides an anti-cancer compound for use in a method of treating a disease characterised by bone marrow neovasculature, such as leukaemia, myelodysplastic syndromes, or multiple myeloma, the method comprising administering the anti-cancer compound and an antibody that binds an antigen of the bone marrow neovasculature in patients suffering from said disease to an individual in need thereof.

Another aspect of the present invention provides use of an antibody that binds an antigen of the bone marrow neovasculature in patients suffering from a disease characterised by bone marrow neovasculature, such as leukaemia, myelodysplastic syndromes, or multiple myeloma, in the manufacture of a medicament for use in a method of treating said disease, the method comprising administering the antibody and an anti-cancer compound.

Another aspect of the present invention provides use of an anti-cancer compound in the manufacture of a medicament for use in a method of treating a disease characterised by bone marrow neovasculature, such as leukaemia, myelodysplastic syndromes, or multiple myeloma, the method comprising administering the anti-cancer compound and an antibody that binds an antigen of the bone marrow neovasculature in patients suffering from said disease.

Another aspect of the present invention provides a method of treating a disease characterised by bone marrow neovasculature, such as leukaemia, myelodysplastic syndromes, or multiple myeloma, comprising administering a therapeutically effective amount of an antibody and an anti-cancer compound to an individual in need thereof, wherein the antibody binds an antigen of the bone marrow neovasculature in patients suffering from said disease.

Another aspect of the present invention provides an antibody that binds an antigen of the bone marrow neovasculature in patients suffering from a disease characterised by bone marrow neovasculature, such as leukaemia, myelodysplastic syndromes, or multiple myeloma, for use in a method of diagnosis of said disease.

Another aspect of the present invention provides use of an antibody that binds an antigen of the bone marrow neovasculature in patients suffering from a disease characterised by bone marrow neovasculature, such as leukaemia, myelodysplastic syndromes, or multiple myeloma, in the manufacture of a diagnostic agent for diagnosing said disease.

Another aspect of the present invention provides use of an antibody that binds an antigen of the bone marrow neovasculature in patients suffering from a disease characterised by bone marrow neovasculature, such as leukaemia, myelodysplastic syndromes, or multiple myeloma, for in vitro detection or diagnosis of said disease.

Another aspect of the present invention provides a method of detecting or diagnosing a disease characterized by bone marrow neovasculature, such as leukaemia, myelodysplastic syndromes, or multiple myeloma, in an individual, wherein the method comprises:
   administering an antibody that binds an antigen of the bone marrow neovasculature in said patients to the individual; and
   detecting binding of the antibody to bone marrow neovasculature in the individual.

Another aspect of the present invention provides a method of detecting or diagnosing a disease characterized by bone marrow neovasculature, such as leukaemia, myelodysplastic syndromes, or multiple myeloma, in an individual, wherein the method comprises:
   administering an antibody that binds an antigen of the bone marrow neovasculature in these patients to the individual; and
   determining the presence or absence of the antibody in the bone marrow of the individual,
   wherein the presence of the antibody in the bone marrow neovasculature of the individual indicates that the individual has said disease.

Another aspect of the present invention provides an in vitro method of detecting or diagnosing a disease characterized by bone marrow neovasculature, such as leukaemia, myelodysplastic syndromes, or multiple myeloma, in an individual, wherein the method comprises:
   applying an antibody that binds an antigen of the bone marrow neovasculature in said patients to a bone marrow sample obtained from the individual; and
   detecting binding of the antibody in the sample,
   wherein binding of the antibody to bone marrow neovasculature in the sample indicates that the individual has said disease.

Another aspect of the present invention provides a method of targeting bone marrow neovasculature, e.g. in vitro, comprising the use of an antibody that binds tenascin-C or the Extra Domain-A (ED-A) isoform of fibronectin.

Another aspect of the present invention provides use of an antibody that binds tenascin-C or the Extra Domain-A (ED-A) isoform of fibronectin for targeting bone marrow neovasculature, e.g. in vitro.

Another aspect of the present invention provides use of an antibody that binds tenascin-C or the Extra Domain-A (ED-A) isoform of fibronectin for the manufacture of a medicament for use in targeting bone marrow neovasculature.

Another aspect of the present invention provides an antibody that binds tenascin-C or the Extra Domain-A (ED-A) isoform of fibronectin for use in a method of treatment or diagnosis comprising targeting bone marrow neovasculature.

Diseases characterized by the presence of neovascular structures in the bone marrow include leukaemia, myelodysplastic syndromes (also referred to as preleukaemias), and multiple myeloma. Exemplary leukaemias include acute and chronic leukaemias. For example, a leukaemia as referred to herein may be a myeloid or a lymphocytic leukaemia. Preferably, a leukaemia as referred to herein is acute myeloid leukaemia (AML).

Myelodysplastic syndromes are bone marrow stem cell disorders characterized by ineffective production (or dysplasia) of myeloid blood cells and risk of transformation to acute myelogenous leukemia (AML).

Multiple myeloma is also known as myeloma, plasma cell myeloma, or Kahler's disease and is a cancer which affects the plasma cells in the bone marrow. All of the above diseases are known to be characterized by neovessels, or angiogenesis, in the bone marrow.

Bone marrow neovasculature as referred to herein may be vascular structures found in the bone marrow of patients suffering from a disease characterized by bone marrow angiogenesis such as leukaemia, myelodysplastic syndromes, or multiple myeloma. These vascular structures may not be found in the bone marrow of healthy individuals, or may be found in the bone marrow of healthy individuals but to a lesser extent than in individuals suffering from such a disease. Thus, the disease may be a disease characterized by increased bone marrow neovasculature.

Antibodies for use in the present invention may bind an antigen expressed in bone marrow neovasculature. The bone marrow neovasculature may be the neovasculature present in the bone marrow of a patient suffering from a disease characterised by bone marrow angiogenesis, e.g. leukaemia, myelodysplastic syndromes or multiple myeloma. Preferably an antibody for use in the present invention binds an antigen of the bone marrow neovasculature in leukaemia patients. Most preferred for use in the present invention are antibodies that bind an antigen of the bone marrow neovasculature in acute myeloid leukaemia (AML) patients.

The antigen may be an antigen which is differentially expressed in bone marrow neovasculature compared with normal tissue. For example, the antigen may be an isoform of a protein, wherein the isoform is differentially expressed in bone marrow neovasculature compared with normal tissue. Normal tissue in this context may be healthy tissues, i.e. tissues not affected by disease. Where the antigen is an antigen of the bone marrow neovasculature in patients suffering from a disease characterised by bone marrow angiogenesis, e.g. leukaemia patients, such as e.g. acute myeloid leukaemia patients, patients with myelodysplastic syndromes or multiple myeloma, the antigen may be differentially expressed in the bone marrow neovasculature of these patients compared with other tissues of these patients. For example, the antigen may be differentially expressed in the bone marrow neovasculature of these patients compared with other bone marrow tissues of these patients, such as other bone marrow blood vessels.

The antigen may be an antigen (e.g. an isoform of a protein) that is differentially expressed in the bone marrow neovasculature of patients suffering from a disease characterised by bone marrow angiogenesis, e.g. leukaemia patients, such as e.g. acute myeloid leukaemia patients, patients with myelodysplastic syndromes or multiple myeloma, compared with normal tissues, e.g. bone marrow tissues, of healthy individuals. Normal tissue in this context are healthy tissues, i.e. tissues not affected by disease. For example, the antigen may be an antigen that is differentially expressed in the bone marrow neovasculature of these patients compared with the bone marrow blood vessels found in healthy individuals.

Differential expression in this context may mean that the antigen is expressed in bone marrow neovasculature and not expressed, or not significantly expressed, in normal tissue. Alternatively, differential expression may mean that expression of the antigen in bone marrow neovasculature is higher, e.g. significantly higher, than in normal tissue. The level of expression of an antigen in a relevant tissue may be measured using, for example, ELISA, Western Blotting, or Mass Spectrometry. All of these methods are well established in the art. "Significantly" in the context of antigen expression may mean statistically significantly, e.g. when measured using a Student T-test. Where a Student T-test is used, a p-value below e.g. 0.1, 0.05, or 0.01 (depending on the threshold chosen for statistical significance), indicates that the level of expression of the antigen in question is significantly different in the tissues that are being compared. Thus, where the level of expression of an antigen in bone marrow neovasculature and normal tissue is compared using a Student T-test, a p-value below e.g. 0.1, 0.05, or 0.01 indicates that the level of expression of the antigen differs significantly between the two tissues. Similarly, an antigen is not significantly expressed in a tissue if the level of expression of the antigen in said tissue is not statistically different from a negative control. Where a Student T-test is used to compare the level of expression in a tissue with a negative control, a p-value of 0.1 or above, 0.05 or above, or 0.01 or above (again depending on the threshold chosen for statistical significance), indicates that the level of expression of the antigen in the tissue question does not differ significantly from the negative control, and hence is not significantly expressed in said tissue.

The antigen may be an antigen of the extracellular matrix, e.g. the subendothelial extracellular matrix, of bone marrow neovasculature. The antigen may be expressed on cells of the bone marrow neovasculature.

Examples of suitable antigens include tenascin-C and the Extra Domain-A (ED-A) isoform of fibronectin. Preferred antigens are the Extra Domain-A (ED-A) of fibronectin and the tenascin-C large isoform, in particular the A1 domain of the tenascin-C large isoform.

Thus, in one example, an antibody for use in the invention may bind to an isoform of fibronectin that is differentially expressed in the bone marrow neovasculature in patients suffering from a disease characterised by bone marrow angiogenesis, e.g. leukaemia patients, such as e.g. acute myeloid leukaemia patients, patients with myelodysplastic syndromes or multiple myeloma as described above. For example, an antibody for use in the invention may bind the Extra Domain-A (ED-A) isoform of fibronectin. The antibody may bind preferentially to the Extra Domain-A (ED-A) isoform of fibronectin compared with other isoforms of fibronectin. Preferred antibodies for use in the invention include antibodies which bind to the Extra Domain-A (ED-A) of fibronectin.

Alternatively, an antibody for use in the invention may bind to an isoform of tenascin-C that is differentially expressed in the bone marrow neovasculature in patients suffering from a disease characterised by bone marrow angiogenesis, e.g. leukaemia patients, such as e.g. acute myeloid leukaemia patients, patients with myelodysplastic syndromes or multiple myeloma as described above. For example, an antibody for use in the invention may bind to the tenascin-C large isoform. The antibody may bind preferentially to tenascin-C large isoform relative to tenascin-C small isoform. Antibodies for use in the invention may bind a domain of tenascin-C which is subject to alternative splicing and is expressed only in the large isoform, e.g. any of domains A1 to D (see FIG. 1). Preferred antibodies for use in the invention include antibodies which bind the A1 domain of the tenascin-C large isoform.

Human monoclonal antibody fragments specific to tenascin-C are described, for example, in WO2006/050834, while human monoclonal antibodies specific for the ED-A isoform of fibronectin are described in WO2008/120101 and also in Villa et al. (2008).

In some embodiments, an antibody for use in the present invention competes for binding to tenascin-C with an antibody comprising the 4A1-F16 VH domain of SEQ ID NO: 2 and the 4A1-F16 VL domain SEQ ID NO: 4. Alternatively, an antibody for use in the present invention may compete for binding to the ED-A isoform of fibronectin with an antibody comprising the F8 (V5L) VH domain of SEQ ID NO. 13 and the F8 (K18R) VL domain of SEQ ID NO. 15.

Competition between antibodies may be assayed easily in vitro, for example using ELISA and/or by tagging a specific reporter molecule to one antibody which can be detected in the presence of other untagged antibody(s), to enable identification of antibodies which bind the same epitope or an overlapping epitope.

In one example, antibody for use in the invention may bind tenascin C (e.g. the A1 domain of the tenascin-C large isoform), or the Extra Domain-A isoform of fibronectin (e.g. the ED-A of fibronectin) with a $K_D$ of at least 1 μM, 100 nM, 50 nM, or 25 nM, when measured using surface plasmon resonance, e.g. using a BIAcore3000 instrument. When measuring affinity, the antibody may be in any convenient format: including small immunoprotein (SIP), scFv, or whole IgG format. A suitable method for determining the affinity of an antibody is described, for example, in Brack et al. (2006).

For example, an antibody for use in the present invention may bind the A1 domain of the tenascin-C large isoform with the same affinity as antibody 4A1-F16-SIP when measured using a BIAcore3000 instrument or with an affinity that is better. Alternatively, an antibody for use in the invention may bind A-FN and/or the ED-A of fibronectin with the same affinity as antibody F8-SIP (V5L/K18R) when measured using surface plasmon resonance, e.g. using a BIAcore3000 instrument, or with an affinity that is better.

The antibody 4A1-F16 has VH and VL domain amino acid sequences and CDRs as shown in the appended sequence listing.

A suitable antibody for use in the present invention may comprise an antibody antigen binding site comprising a VH domain and a VL domain,
the VH domain comprising a VH CDR1 of SEQ ID NO. 5, a VH CDR2 of SEQ ID NO. 6 and a VH CDR3 of SEQ ID NO. 7; and
the VL domain comprising a VL CDR1 of SEQ ID NO. 8, a VL CDR2 of SEQ ID NO. 9 and a VL CDR3 of SEQ ID NO. 10.

In some preferred embodiments, an antibody for use in the present invention may comprise an antibody antigen binding site comprising the 4A1-F16 VH domain of SEQ ID NO. 2 and the 4A1-F16 VL domain of SEQ ID NO. 4.

Antibody F8 (V5L/K18R) has VH and VL domain amino acid sequences and CDRs as shown in the appended sequence listing.

A suitable antibody for use in the present invention may comprise an antibody antigen binding site comprising a VH domain and a VL domain,
the VH domain comprising a VH CDR1 of SEQ ID NO:16, a VH CDR2 of SEQ ID NO:17, and a VH CDR3 of SEQ ID NO:18;
the VL domain comprising a VL CDR1 of SEQ ID NO: 19, a VL CDR2 of SEQ ID NO:20, and a VL CDR3 of SEQ ID NO:21.

In some preferred embodiments, the antibody for use in the present invention may comprise an antibody antigen binding site comprising the F8 (V5L) VH domain of SEQ ID NO:13 and the F8 (K18R) VL domain of SEQ ID NO:15.

A number of antibody molecule formats are known and any suitable format may be used for an antibody for use in the invention.

In some embodiments, an antibody for use in the invention may be or comprise a single chain Fv (scFv), comprising a VH domain and a VL domain joined via a peptide linker. The skilled person may select an appropriate length and sequence of linker, e.g. at least 5 or at least 10 amino acids in length, up to about 15, up to about 20 or up to about 25 amino acids in length. For example, the linker may have the amino acid sequence shown in SEQ ID NO:11 or SEQ ID NO:22.

In embodiments, an antibody for use in the present invention may be a mini-immunoglobulin or small immunoprotein (SIP) comprising a single chain Fv (scFv), e.g. as described in (Li et al., 1997). An SIP may comprise an scFv molecule fused to the CH4 domain of the human IgE secretory isoform IgE-S2 ($\epsilon_{S2}$-CH4; Batista et al., 1996) forming an homo-dimeric mini-immunoglobulin antibody molecule. The CH4 domain may have the amino acid sequence shown in SEQ ID NO:24 and may be linked to the VL domain via a peptide linker. A suitable peptide linker is shown in SEQ ID NO:23.

In some embodiments, an antibody for use in the present invention may be a whole IgG antibody molecule, e.g. a whole IgG1 antibody molecule.

Variants of the VH and VL domains and CDRs described herein may also be employed in antibodies for use in the present invention. Suitable variants can be obtained by means of methods of sequence alteration or mutation and screening.

Particular variants for use as described herein may include one or more amino acid sequence alterations (addition, deletion, substitution and/or insertion of an amino acid residue), maybe less than about 20 alterations, less than about 15 alterations, less than about 10 alterations or less than about 5 alterations, 4, 3, 2 or 1. Alterations may be made in one or more framework regions and/or one or more CDRs. In particular, alterations may be made in VH CDR1, VH CDR2 and/or VH CDR3, especially VH CDR3.

In some embodiments, the 4A1-F16 VL domain of SEQ ID NO: 4 may lack the Serine at position 1.

In some preferred embodiments an antibody for use in the present invention is conjugated to a bioactive molecule, such as a cytokine (e.g. IL2), cytotoxic agent, photosensitizer, or therapeutic radioisotope.

IL2-containing immunocytokines have previously been shown to be capable of eradicating tumours and lymphomas in mouse models of cancer when used alone or in combination with other therapeutic agents such as chemotherapy or intact antibodies (Schliemann et al., 2009; Marlind, et al., 2008; Menrad et al., 2005; and Carnemolla et al., 2002).

Thus, in some embodiments an antibody for use in the present invention may be conjugated to a cytokine, e.g. interleukin 2 (IL2), to form an antibody-cytokine conjugate. The main attraction of using such immunocytokines is the activation of immune cells (e.g., natural killer [NK] cells) which may allow the last surviving blast cells to be eradicated, thereby making the difference between a patient suffering relapses after treatment and a cure.

As NK cells are mainly responsible for the therapeutic action of antibody-IL2 conjugates, the activity of such molecules can be studied in tumour-bearing immunocompromised mice. For example, mouse models of human leukaemia can be used to study the in vivo targeting potential and the therapeutic activity of antibody-IL2 conjugates in the treatment of leukaemia. A suitable mouse model for human leukaemia employs the HL-60 leukaemia cell line in nude mice, as disclosed in Potter et al. (1984).

Interleukin-2 (IL2) is a secreted cytokine which is involved in immunoregulation and the proliferation of T and B lymphocytes. IL2 has been shown to have a cytotoxic effect on tumour cells and recombinant human IL2 (aldesleukin: Proleukin™) has FDA approval for treatment of metastatic renal carcinoma and metastatic melanoma. The sequence of human IL2 is set out in SEQ ID NO: 27 and publicly available under sequence database reference NP_000577.2 GI: 28178861.

In some preferred embodiments, the IL2 moiety of the antibody-IL2 conjugate comprises a sequence which has at least 90% sequence identity, at least 95% sequence identity or at least 98% sequence identity to the mature human IL2 sequence set out in SEQ ID NO: 27.

Sequence identity is commonly defined with reference to the algorithm GAP (Wisconsin GCG package, Accelerys Inc, San Diego USA). GAP uses the Needleman and Wunsch algorithm to align two complete sequences that maximizes the number of matches and minimizes the number of gaps. Generally, default parameters are used, with a gap creation penalty=12 and gap extension penalty=4. Use of GAP may be preferred but other algorithms may be used, e.g. BLAST (which uses the method of Altschul et al. (1990) *J. Mol. Biol.* 215: 405-410), FASTA (which uses the method of Pearson and Lipman (1988) *PNAS USA* 85: 2444-2448), or the Smith-Waterman algorithm (Smith and Waterman (1981) *J. Mol. Biol.* 147: 195-197), or the TBLASTN program, of Altschul et al. (1990) supra, generally employing default parameters. In particular, the psi-Blast algorithm (Nucl. Acids Res. (1997) 25 3389-3402) may be used.

In some especially preferred embodiments, the IL2 moiety of the antibody-IL2 conjugate comprises the sequence of mature human IL2 set out in SEQ ID NO: 27.

The IL2 moiety may be fused upstream (N-terminal) or downstream (C-terminal) of the antibody or polypeptide component thereof.

The IL2 moiety may be connected or attached to the antibody moiety of the antibody-IL2 conjugate by any suitable covalent or non-covalent means. In preferred embodiments, the antibody-IL2 conjugate may be a fusion protein comprising IL2 and the antibody or a polypeptide component thereof (e.g. a heavy chain or a light chain of an antibody or multi-chain antibody fragment, such as a Fab). Thus, for example, the IL2 moiety may be fused to a VH domain or VL domain of the antibody. Typically the antibody, or component thereof, and IL2 moiety are joined via a peptide linker, e.g., a peptide of about 5-25 residues, e.g. 10-20 residues, preferably about 15 residues. Suitable examples of peptide linkers are well known in the art. In some embodiments, a linker may have an amino acid sequence as set out in SEQ ID NO: 28. Normally, the linker has an amino acid sequence comprising one or more tandem repeats of a motif. Typically the motif is a five residue sequence, and preferably at least 4 of the residues are Gly or Ser. Where four of the five residues is Gly or Ser, the other residue may be Ala. More preferably each of the five residues is Gly or Ser. Preferred motifs are GGGGS (SEQ ID NO: 33), SSSSG (SEQ ID NO: 34), GSGSA (SEQ ID NO: 35) and GGSGG (SEQ ID NO: 36). Preferably, the motifs are adjacent in the sequence, with no intervening nucleotides between the repeats. The linker sequence may comprise or consist of between one and five, preferably three or four, repeats of the motif. For example, a linker with three tandem repeats may have one of the amino acid sequences shown in SEQ ID NOs. 29 to 32.

Antibody-drug conjugates are known to be useful for selectively delivering a cytotoxic agent to a target such as a tumour-associated antigen (Carter et al., 2008). Such conjugates allow the delivery of cytotoxic agents directly to the affected tissues, thereby avoiding the disadvantages associated with conventional chemotherapy. For example, it has previously been shown that antibodies such as F16 or F8 can be coupled to cytotoxic drugs and can localize with extraordinary efficiency and selectivity around tumour blood vessels.

Thus, in some embodiments an antibody for use in the invention may be conjugated to a cytotoxic agent. Exemplary cytotoxic agents include cytotoxic agents which are suitable for treating cancer. For example a cytotoxic agent may be suitable for treating a disease characterized by bone marrow neovasculature, such as leukaemia myelodysplastic syndromes, or multiple myeloma, e.g. AML.

Preferred cytotoxic agent include potent cytotoxic agent of relatively simple chemical structure to facilitate manufacture. The use of potent cytotoxic agents is preferred because of the difference in molecular weight between antibodies and cytotoxic agents (Carter et al., 2008). A potent cytotoxic agent may be a cytotoxic agent capable of killing tumour cells at sub-nanomolar concentrations. Suitable, cytotoxic agents which may be conjugated to an antibody for use in the present invention include dolastatins, vinblastines, epothilones, tubulysins, and derivatives and analogues thereof.

Dolastatins are a family of antiproliferative peptides which inhibit the growth and reproduction of target cells and induce apoptosis in a variety of malignant cell types. Exemplary dolastatins include dolastatin-10 and dolastatin-15, and their derivatives, which have been shown to have particularly strong antiproliferative bioactivity (de Arruda et al., 1995). One preferred dolastatin derivative is cemadotin which is a dolastatin-15 analogue. In preferred embodiments, the antibody-dolastatin conjugate may be a fusion protein comprising the dolastatin and the antibody or a polypeptide component thereof (e.g. a heavy chain or a light chain of an antibody or multi-chain antibody fragment, such as a Fab. Thus, for example, the dolastatin moiety may be fused to a VH domain or VL domain of the antibody.

Vinblastine is a chemical analogue of vincristine which is used in a number of chemotherapy regimens including treatment for Hodgkin lymphoma. Potent analogues of vinbalstine are described in Barnett et al. (1978) and include 4-desacetyl-3-vinblastine monohydrazide.

Both 4-desacetyl-3-vinblastine monohydrazide and cemadotin act on microtubuli with a similar mechanism of action and are capable of killing target tumour cells and endothelial cells in the picomolar concentration range (de Arruda et al., 1995; Barnett et al., 1978; Reddy et al., 2007; Ray et al., 2007; and Leamon et al., 2007).

Epothilones are a class of cytotoxic molecules which have been shown to have antitumour activity. Exemplary epothilones include ixabepilone, epothilone B, and epothilone D.

Tubulysins are another family of antiproliferative agents which are leading candidates for the development of anti-cancer agents. Exemplary tubulysins include tubulysin A and tubulysin D. Exemplary tubulysin derivatives are described in Neri et al. (2006), Sani et al. (2007) and Patterson et al. (2007).

In some embodiments the antibody for use in the invention may be conjugated to a cytotoxic agent comprising a terminal maleimido group. Maleimido groups can be used for the site-specific drug conjugation to unique reactive cysteine residues present in the antibodies described herein (Borsi et al., 2002; Berndorff et al., 2006). Most preferably, a cleavable linker is present between the cytotoxic agent and the maleimido moiety.

It has previously demonstrated how the intraluminal blood coagulation in tumour neo-vasculature, caused by the antibody-mediated delivery of pro-coagulant factors such as a truncated version of tissue factor, can lead to rapid tumour cell death. Thus, in some embodiments an antibody for use in the invention may be conjugated to a pro-coagulant factor such as a truncated version of tissue factor. Such conjugates have been previously described in Nilsson et al. (2001).

Vascular targeting antibodies have also previously been shown to be suitable for depositing photosensitizers around neo-vasculature of tumours in vivo, thus mediating endothelial cell damage and intraluminal blood coagulation upon irradiation, followed by tumour cell death (Birchler et al., 1999; Fabbrini et al., 2006). Specifically, it has been shown that photosensitizers can efficiently generate singlet oxygen outside endothelial cells and kill tumour cells indirectly. Prior to these experiments, it was generally believed that antibody-photosensitizer conjugates needed to be internalized by the target cells, in order to mediate a toxic effect upon irradiation.

Thus, in some embodiments an antibody for use in the invention may be conjugated to a photosensitizer. Exemplary photosensitizers which may be conjugated to an antibody for use in the present invention are described in detail in WO01/62800 and include tin (IV) chlorine e6 and derivatives thereof.

Antibodies conjugated to therapeutic radionuclides have also previously been shown to be effective in the treatment of cancer (Tijink et al., J Nucl Med. 47(7):1070-4, 2006). Thus in some embodiments an antibody for use in the present invention may be conjugated to a therapeutic radionuclide. Exemplary therapeutic radionuclides include $^{131}$I, $^{90}$Y, $^{124}$I, $^{211}$At, $^{77}$Br, and $^{76}$BR. Preferably, the therapeutic radionuclide is $^{131}$I or $^{90}$Y.

The bioactive molecule may be connected or attached to the antibody moiety by any suitable covalent or non-covalent means. In preferred embodiments the bioactive molecule is conjugated to the antibody by a cleavable linker, thereby allowing the bioactive molecule to be released. For example, the linker may allow release of the bioactive molecule into the sub-endothelial extracellular matrix present in the bone marrow of a patient suffering from a disease characterized by bone marrow neovasculature thereby allowing the drug to diffuse to the bone marrow neovasculature and, where the disease is leukaemia, potentially also to neighbouring blasts.

Suitable cleavable linkers include Schiff bases, peptide linkers cleavable by proteases and stabilized esters. All of these linkers are well known in the art. Exemplary Schiff base linkers are described, for example, in U.S. Pat. No. 5,633,351. Preferred cleavable linkers exhibit reaction half-lives in the 5-20 hour range.

An antibody or antibody conjugate for use in the present invention may be administered to an individual in need thereof together with an anti-cancer compound, e.g. an anti-leukaemia compound.

Anti-cancer compounds are cytotoxic compounds which inhibit the growth, division and/or proliferation of cancer cells. Anti-cancer compounds may, in some circumstances, have an effect on normal non-cancer cells in a patient. An anti-cancer compound may, for example, be a compound suitable for treating leukaemia. Where the patient is an acute myeloid leukaemia patient, the compound may be a compound suitable for treating acute myeloid leukaemia.

In some embodiments of the invention, the anti-cancer compound may be selected from the group of: alkylating agents, anti-metabolites, plant alkaloids and terpenoids, topoisomerase inhibitors, antitumour antibiotics, monoclonal antibodies, and corticosteroids. Examples of alkylating agents include cyclophosphamide, cisplatin, chlorambucil, carboplatin, and oxaliplatin. Examples of anti-metabolites include methotrexate, purine analogues such as cladribine, fludarabine, tioguanine and pentostatin, and pyrimidine analogues such as cytarabine, 5-fluorouracil, and floxuridine. Examples of plant alkaloids and terpenoids include vinca alkaloids, such as vincristine, vinblastine, vinorelbine, and vindesine; chemotherapeutic agents derived from podophyllotoxin such as etoposide phosphate and teniposide taxanes; and taxanes, which include paclitaxel and docetaxel. Examples of topoisomerase inhibitors include type I topoisomerase inhibitors such as camptothecins and type II topoisomerase inhibitors such as amsacrine, etoposide, etoposide phosphate, and teniposide. Examples of antitumour antibiotics include anthracyclines, such as doxorubicin and epirubicin, actinomycins, and bleomycin. Examples of monoclonal antibodies include rituximab, and examples of corticosteroids include prednisone and prednisolone.

Exemplary anti-cancer compounds suitable for treating leukaemia include: anthracyclines, cytarabine, vincristine, L-asparaginase, cyclophosphamide, methotrexate and 6-mercaptopurine, chlorambucil, cyclophosphamide, corticosteroids, such as prednisone and prednisolone, imatinib, cladribine, pentostatin, rituximab, chlorambucil, and doxorubicin.

Preferred anti-cancer compounds include anthracyclines and cytarabine. These anti-cancer compounds are suitable for treating AML.

For example, in some embodiments of the invention, an antibody or antibody conjugate (e.g. an antibody-cytokine conjugate) may be administered to an individual in need thereof in combination with chemotherapy or IgG-based immunotherapy. For example, anti-CD33 antibodies are currently being investigated for the treatment of AML in Phase IIb clinical trials. Suitable anti-CD33 antibodies are described, for example in Feldman et al. (2003), Feldman et al. (2005) and Kobayashi et al. (2009). In addition, IgG based anti-CD123 antibodies are also being investigated in the treatment of AML (Jin et al., 2009). Thus, in one example, IgG-based immunotherapy may involve treatment with an anti-CD33 or anti-CD123 antibody.

In some embodiments an antibody for use in the invention may be labelled with a detectable or functional label. Antibodies labelled with a detectable label, may be used diagnostically in vivo, ex vivo or in vitro, and/or therapeutically.

A detectable label may be any molecule that produces or can be induced to produce a signal, including but not limited to fluorescers, radiolabels, enzymes, chemiluminescers or photosensitizers. Thus, binding may be detected and/or measured by detecting fluorescence or luminescence, radioactivity, enzyme activity or light absorbance. Detectable labels may be attached to antibodies for use in the invention using conventional chemistry known in the art.

There are numerous methods by which the label can produce a signal detectable by external means, for example, by visual examination, electromagnetic radiation, heat, and chemical reagents. The label can also be bound to another specific binding member that binds the antibody for use in the invention, or to a support.

Administration of an antibody, antibody conjugate, anti-cancer compound and compositions comprising one or more of these molecules is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage etc, is within the responsibility of general practitioners and other medical doctors.

The precise dose will depend upon a number of factors, the size and location of the area to be treated, the precise nature of the antibody (e.g. whole antibody, fragment or diabody). A typical antibody, or antibody conjugate, dose will be in the range 0.5 mg to 100 g for systemic applications, and 10 μg to 1 mg for local applications. The antibody, or antibody moiety of the conjugate, may be an scFv, SIP or whole antibody. Where the antibody or antibody moiety is a whole antibody, it is preferably the IgG isotype, e.g. IgG1. This is a dose for a single treatment of an adult patient, which may be proportionally adjusted for children and infants, and also adjusted for other antibody formats in proportion to molecular weight. Appropriate doses and regimens for anti-cancer compounds are well known in the art.

Treatments may be repeated at daily, twice-weekly, weekly or monthly intervals, at the discretion of the physician.

Where an antibody (or antibody conjugate) and an anti-cancer compound are administered to a patient, these may be administered sequentially or simultaneously in accordance with any suitable regimen.

An antibody, antibody conjugate or anti-cancer compound may be administered to an individual in the form of a pharmaceutical composition, which may comprise at least one component in addition to the active compound. Where both an antibody (or antibody conjugate) and an anti-cancer compound are administered to a patient, these may be formulated in separate pharmaceutical compositions or, where appropriate, in the same pharmaceutical composition.

Suitable components include a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous.

Apart from antibodies, there are also other types of binding members which are also suitable for use in the present invention. Thus, in one example, a non-antibody binding member may be used in an embodiment of the present invention instead of an antibody. Suitable non-antibody binding members for use in the present invention may comprise an antigen-binding site, normally provided by one or more CDRs, e.g. a set of CDRs, in a non-antibody protein scaffold, as described in more detail below.

Terminology

Antibody

This describes an immunoglobulin whether natural or partly or wholly synthetically produced. The term also covers any polypeptide or protein comprising an antibody antigen-binding site. Antibody fragments that comprise an antibody antigen-binding site include, but are not limited to, molecules such as Fab, Fab', Fab'-SH, scFv, Fv, dAb and Fd. Various other antibody molecules including one or more antibody antigen-binding sites have been engineered, including for example $Fab_2$, $Fab_3$, diabodies, triabodies, tetrabodies, minibodies and small immunoproteins (SIPs). Antibody molecules and methods for their construction and use are described in Holliger & Hudson, *Nature Biotechnology* 23(9):1126-1136 2005.

It is possible to take monoclonal and other antibodies and use techniques of recombinant DNA technology to produce other antibodies or chimeric molecules that bind the target antigen. Such techniques may involve introducing DNA encoding the immunoglobulin variable region, or the CDRs, of an antibody to the constant regions, or constant regions plus framework regions, of a different immunoglobulin. See, for instance, EP-A-184187, GB 2188638A or EP-A-239400, and a large body of subsequent literature. A hybridoma or other cell producing an antibody may be subject to genetic mutation or other changes, which may or may not alter the binding specificity of antibodies produced.

As antibodies can be modified in a number of ways, the term "antibody molecule" should be construed as covering any binding member or substance having an antibody antigen-binding site with the required specificity and/or binding to antigen. Thus, this term covers antibody fragments and derivatives, including any polypeptide comprising an antibody antigen-binding site, whether natural or wholly or partially synthetic. Chimeric molecules comprising an antibody antigen-binding site, or equivalent, fused to another polypeptide (e.g. derived from another species or belonging to another antibody class or subclass) are therefore included. Cloning and expression of chimeric antibodies are described in EP-A-0120694 and EP-A-0125023, and a large body of subsequent literature.

Preferably, the antibody molecules used in the invention are human or humanised antibody molecules.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989); McCafferty et al (1990) Nature, 348, 552-554; Holt et al (2003) Trends in Biotechnology 21, 484-490), which consists of a VH or a VL domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (viii) bispecific single chain Fv dimers (PCT/US92/09965) and (ix) "diabodies", multivalent or multispecific fragments constructed by gene fusion (WO94/13804; Holliger, P. et al, Proc. Natl. Acad. Sci. USA 90 6444-6448, 1993). Fv, scFv or diabody molecules may be stabilized by the incorporation of disulphide bridges linking the VH and VL domains (Reiter, Y. et al, Nature Biotech, 14, 1239-1245, 1996). A single chain Fv (scFv) may be comprised within a mini-immunoglobulin or small immunoprotein (SIP), e.g. as described in (Li et al., 1997). An SIP may comprise an scFv molecule fused to the CH4 domain of the human IgE secretory isoform IgE-S2 ($\epsilon_{S2}$-CH4; Batista et al., 1996) forming an homo-dimeric mini-immunoglobulin antibody molecule. Further, minibodies comprising a scFv joined to a CH3 domain may also be made (Hu, S. et al, Cancer Res., 56, 3055-3061, 1996). Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

Qui et al., *Nat. Biotechnol.* 25:921-929 (2007) described antibody molecules containing just two CDRs linked by a framework region. CDR3 from the VH or VL domain was linked to the CDR1 or CDR2 loop of the other domain. Linkage was through the C terminus of the selected CDR1 or CDR2 to the N terminus of the CDR3, via a FR region. Qui et al. selected the FR region having the fewest hydrophobic patches. The best combination for the antibody tested was found to be VL CDR1 linked by VH FR2 to VH CDR3 (VHCDR1-VHFR2-VLCDR3). At a molecular weight of around 3 kDa, these antibody molecules offer advantages in terms of improved tissue penetration as compared with full immunoglobulins (approx. 150 kDa) or scFv (approx. 28 kDa).

Antibody fragments of the invention can be obtained starting from a parent antibody molecule by methods such as digestion by enzymes e.g. pepsin or papain and/or by cleavage of the disulfide bridges by chemical reduction. In another manner, the antibody fragments comprised in the present invention can be obtained by techniques of genetic recombination likewise well known to the person skilled in the art or else by peptide synthesis by means of, for example, automatic peptide synthesizers, such as those supplied by the company Applied Biosystems, etc., or by nucleic acid synthesis and expression. Functional antibody fragments according to the present invention include any functional fragment whose half-life is increased by a chemical modification, especially by PEGylation, or by incorporation in a liposome.

A dAb (domain antibody) is a small monomeric antigen-binding fragment of an antibody, namely the variable region of an antibody heavy or light chain (Holt et al (2003) Trends in Biotechnology 21, 484-490). VH dAbs occur naturally in camelids (e.g. camel, llama) and may be produced by immunizing a camelid with a target antigen, isolating antigen-specific B cells and directly cloning dAb genes from individual B cells. dAbs are also producible in cell culture. Their small size, good solubility and temperature stability makes them particularly physiologically useful and suitable for selection and affinity maturation. Camelid VH dAbs are being developed for therapeutic use under the name "Nanobodies™". An antibody molecule of the present invention may be a dAb. The antibody molecule comprise a VH or VL domain substantially as set out herein, or a VH or VL domain comprising a set of CDRs substantially as set out herein.

Bispecific or bifunctional antibodies form a second generation of monoclonal antibodies in which two different variable regions are combined in the same molecule (Holliger and Bohlen, Cancer and metastasis rev. 18: 411-419, 1999). Their use has been demonstrated both in the diagnostic field and in the therapy field from their capacity to recruit new effector functions or to target several molecules on the surface of tumour cells. Where bispecific antibodies are to be used, these may be conventional bispecific antibodies, which can be manufactured in a variety of ways (Holliger, P. and Winter G. Current Opinion Biotechnol 4, 446-449, 1993), e.g. prepared chemically or from hybrid hybridomas, or may be any of the bispecific antibody fragments mentioned above. These antibodies can be obtained by chemical methods (Glennie M J et al., 1987 J. Immunol. 139, 2367-2375; Repp R. et al., 1995 J. Hemat. 377-382) or somatic methods (Staerz U. D. and Bevan M. J. 1986 PNAS 83; Suresh M. R. et al., 1986 Method Enzymol. 121: 210-228) but likewise and preferentially by genetic engineering techniques which allow the heterodimerization to be forced and thus facilitate the process of purification of the antibody sought (Merchand et al., 1998 Nature Biotech. 16:677-681). Examples of bispecific antibodies include those of the BiTE™ technology in which the binding domains of two antibodies with different specificity can be used and directly linked via short flexible peptides. This combines two antibodies on a short single polypeptide chain. Diabodies and scFv can be constructed without an Fc region, using only variable domains, potentially reducing the effects of anti-idiotypic reaction.

Bispecific antibodies can be constructed as entire IgG, as bispecific Fab'2, as Fab'PEG, as diabodies or else as bispecific scFv. Further, two bispecific antibodies can be linked using routine methods known in the art to form tetravalent antibodies.

Bispecific diabodies, as opposed to bispecific whole antibodies, may also be particularly useful because they can be readily constructed and expressed in *E. coli*. Diabodies (and many other polypeptides, such as antibody fragments) of appropriate binding specificities can be readily selected using phage display (WO94/13804) from libraries. If one arm of the diabody is to be kept constant, for instance, with a specificity directed against the antigen of the tumour neovasculature, then a library can be made where the other arm is varied and an antibody of appropriate specificity selected. Bispecific whole antibodies may be made by alternative engineering methods as described in Ridgeway et al., 1996 (Ridgeway, J. B. B. et al, Protein Eng., 9, 616-621, 1996).

Various methods are available in the art for obtaining antibodies against a target antigen. The antibodies may be monoclonal antibodies, especially of human, murine, chimeric or humanized origin, which can be obtained according to the standard methods well known to the person skilled in the art.

In general, for the preparation of monoclonal antibodies or their functional fragments, especially of murine origin, it is possible to refer to techniques which are described in particular in the manual "Antibodies" (Harlow and Lane, Antibodies: A Laboratory Manual, Cold Spring Harbor) or to the technique of preparation from hybridomas described by Köhler and Milstein (Köhler and Milstein, Nature, 256: 495-497, 1975).

Monoclonal antibodies can be obtained, for example, from an animal cell immunised against the target antigen or one of its fragments containing the epitope recognised by the monoclonal antibodies. Suitable fragments and peptides or polypeptides comprising them are described herein, and may be used to immunise animals to generate antibodies against a target antigen. Said antigen, or one of its fragments, can especially be produced according to the usual working methods, by genetic recombination starting with a nucleic acid sequence contained in the cDNA sequence coding for the antigen or fragment thereof, by peptide synthesis starting from a sequence of amino acids comprised in the peptide sequence of the antigen and/or fragment thereof.

The monoclonal antibodies can, for example, be purified on an affinity column on which the antigen or one of its fragments containing the epitope recognised by said monoclonal antibodies, has previously been immobilised. More particularly, the monoclonal antibodies can be purified by chromatography on protein A and/or G, followed or not followed by ion-exchange chromatography aimed at eliminating the residual protein contaminants as well as the DNA and the LPS, in itself, followed or not followed by exclusion chromatography on Sepharose gel in order to eliminate the potential aggregates due to the presence of dimers or of other multimers. In one embodiment, the whole of these techniques can be used simultaneously or successively.

In addition to antibody sequences and/or an antigen-binding site, an antibody for use in the present invention may comprise other amino acids, e.g. forming a peptide or polypeptide, such as a folded domain, or to impart to the molecule another functional characteristic in addition to ability to bind antigen. Antibodies for use in the invention may carry a detectable label, or may be conjugated to a toxin or a targeting moiety or enzyme (e.g. via a peptidyl bond or linker). For example, an antibody may comprise a catalytic site (e.g. in an enzyme domain) as well as an antigen binding site, wherein the antigen binding site binds to the antigen and thus targets the catalytic site to the antigen. The catalytic site may inhibit biological function of the antigen, e.g. by cleavage.

Non-Antibody Binding Member

This describes one member of a pair of non-antibody molecules that bind one another. The members of a binding pair may be naturally derived or wholly or partially synthetically produced. One member of the pair of molecules has an area on its surface, or a cavity, which binds to and is therefore complementary to a particular spatial and polar organization of the other member of the pair of molecules. Examples of types of non-antibody binding pairs are biotin-avidin, hormone-hormone receptor, receptor-ligand, enzyme-substrate.

A non-antibody binding member normally comprises a molecule having an antigen-binding site. For example, a non-antibody binding member may be a non-antibody protein that comprises an antigen-binding site.

An antigen binding site may be provided by means of arrangement of complementarity determining regions (CDRs) on non-antibody protein scaffolds such as fibronectin or cytochrome B etc. (Haan & Maggos, 2004; Koide 1998; Nygren 1997), or by randomising or mutating amino acid residues of a loop within a protein scaffold to confer binding specificity for a desired target. Scaffolds for engineering novel binding sites in proteins have been reviewed in detail by Nygren et al. (1997). Protein scaffolds for antibody mimics are disclosed in WO/0034784, which is herein incorporated by reference in its entirety, in which the inventors describe proteins (antibody mimics) that include a fibronectin type III domain having at least one randomised loop. The scaffold may be a human or non-human protein. An advantage of a non-antibody protein scaffold is that it may provide an antigen-binding site in a scaffold molecule that is smaller and/or easier to manufacture than at least some antibody molecules. Small size of a binding member may confer useful physiological properties such as an ability to enter cells, penetrate deep into tissues or reach targets within other structures, or to bind within protein cavities of the target antigen. Use of antigen binding sites in non-antibody protein scaffolds is reviewed in Wess, 2004. Typical are proteins having a stable backbone and one or more variable loops, in which the amino acid sequence of the loop or loops is specifically or randomly mutated to create an antigen-binding site that binds the target antigen. Such proteins include the IgG-binding domains of protein A from *S. aureus*, transferrin, tetranectin, fibronectin (e.g. 10th fibronectin type III domain) and lipocalins as well as gamma-crystalline and other Affilin™ scaffolds (Scil Proteins). Examples of other approaches include synthetic "Microbodies" based on cyclotides—small proteins having intra-molecular disulphide bonds, Microproteins (Versabodies™, Amunix) and ankyrin repeat proteins (DARPins, Molecular Partners).

Similarly to antibodies, a non-antibody binding member for use in the present invention may, in addition to antibody sequences and/or an antigen-binding site, comprise other amino acids, e.g. forming a peptide or polypeptide, such as a folded domain, or to impart to the molecule another functional characteristic in addition to ability to bind antigen. Non-antibody binding members for use in the invention may carry a detectable label, or may be conjugated to a toxin or a targeting moiety or enzyme (e.g. via a peptidyl bond or linker). For example, a non-antibody binding member may comprise a catalytic site (e.g. in an enzyme domain) as well as an antigen binding site, wherein the antigen binding site binds to the antigen and thus targets the catalytic site to the antigen. The catalytic site may inhibit biological function of the antigen, e.g. by cleavage.

Complementary Determining Regions

As noted, CDRs can be carried by antibody and non-antibody scaffolds. The structures and locations of immunoglobulin variable domains may be determined by reference to Kabat 1987, and updates thereof. A number of academic and commercial on-line resources are available to query this database. For example, see Martin (1996) and the associated on-line resource, currently at the web address of bioinf.org.uk/abs/simkab.html.

By CDR region or CDR, it is intended to indicate the hypervariable regions of the heavy and light chains of the immunoglobulin as defined by Kabat et al. (1987), (Kabat 1991a, and later editions). An antibody typically contains 3 heavy chain CDRs and 3 light chain CDRs. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

Among the six short CDR sequences, the third CDR of the heavy chain (HCDR3) has a greater size variability (greater diversity essentially due to the mechanisms of arrangement of the genes which give rise to it). It can be as short as 2 amino acids although the longest size known is 26. CDR length may also vary according to the length that can be accommodated by the particular underlying framework. Functionally, HCDR3 plays a role in part in the determination of the specificity of the antibody (Segal 1974; Amit 1986; Chothia 1987; Chothia 1989; Caton 1990; Sharon 1990a; Sharon 1990b; Kabat et al., 1991b).

Antigen Binding Domain

This describes the part of a molecule that binds to and is complementary to all or part of the target antigen. In an antibody molecule it is referred to as the antibody antigen-binding site, and comprises the part of the antibody that binds to and is complementary to all or part of the target antigen. Where an antigen is large, an antibody may only bind to a particular part of the antigen, which part is termed an epitope. An antibody antigen-binding site may be provided by one or more antibody variable domains. An antibody antigen-binding site may comprise an antibody light chain variable region (VL) and an antibody heavy chain variable region (VH).

WO2006/072620 describes engineering of antigen binding sites in structural (non-CDR) loops extending between beta strands of immunoglobulin domains. An antigen binding site may be engineered in a region of an antibody molecule separate from the natural location of the CDRs, e.g. in a framework region of a VH or VL domain, or in an antibody constant domain e.g. CH1 and/or CH3. An antigen binding site engineered in a structural region may be additional to, or instead of, an antigen binding site formed by sets of CDRs of a VH and VL domain. Where multiple antigen binding sites are present in an antibody molecule, they may bind the same antigen (target antigen), thereby increasing valency of the antibody molecule. Alternatively, multiple antigen binding sites may bind different antigens (the target antigen and one or more another antigen), and this may be used to add effector functions, prolong half-life or improve in vivo delivery of the antibody molecule.

Specific

This may be used to refer to the situation in which one member of a specific binding pair will not show any significant binding to molecules other than its specific binding partner(s). For example, an antibody specific for the ED-A isoform of fibronectin may show little or no binding to other isoforms of fibronectin. An antibody specific for the ED-A domain of fibronectin may show little or no binding to other domains of fibronectin. Similarly, an antibody specific for the tenascin C large isoform may show little or no binding to other isoforms of tenascin C. The term is also applicable where e.g. an antigen binding domain is specific for a particular epitope which is carried by a number of antigens, in which case the specific binding member carrying the antigen binding domain will be able to bind to the various antigens carrying the epitope.

Comprise

This is generally used in the sense of include, that is to say permitting the presence of one or more features or components.

By "substantially as set out" it is meant that the relevant CDR or VH or VL domain of the invention will be either identical or highly similar to the specified regions of which the sequence is set out herein. By "highly similar" it is contemplated that from 1 to 5, preferably from 1 to 4 such as 1 to 3 or 1 or 2, or 3 or 4, substitutions may be made in the CDR and/or VH and/or VL domain.

The structure for carrying a CDR of the invention will generally be that of antibody heavy or light chain sequence or substantial portion thereof in which the CDR is located at a location corresponding to the CDR of naturally occurring VH and VL antibody variable domains encoded by rearranged immunoglobulin genes. The structures and locations of immunoglobulin variable domains and CDRs may be determined by reference to (Kabat, E.A. et al., Sequences of Proteins of Immunological Interest. 4$^{th}$ Edition. US Department of Health and Human Services. 1987, and updates thereof, now available on the Internet (immuno.bme.nwu.edu)).

Fibronectin

Fibronectin (FN) is a glycoprotein and is widely expressed in a variety of normal tissues and body fluids. It is a component of the extracellular matrix (ECM), and plays a role in many biological processes, including cellular adhesion, cellular migration, haemostasis, thrombosis, wound healing, tissue differentiation and oncogenic transformation.

Fibronectin is subject to alternative splicing, and a number of alternative isoforms of fibronectin are known. Extra Domain-A (EDA or ED-A) is also known as ED, extra type III repeat A (EIIIA) or EDI. The sequence of human ED-A has been published by Kornblihtt et al. (1984), Nucleic Acids Res. 12, 5853-5868 and Paolella et al. (1988), Nucleic Acids Res. 16, 3545-3557. The sequence of human ED-A is also available on the SwissProt database as amino acids 1631-1720 (Fibronectin type-III 12; extra domain 2) of the amino acid sequence deposited under accession number P02751. The sequence of mouse ED-A is available on the SwissProt database as amino acids 1721-1810 (Fibronectin type-III 13; extra domain 2) of the amino acid sequence deposited under accession number P11276.

The ED-A isoform of fibronectin (A-FN) contains the Extra Domain-A (ED-A). The sequence of the human A-FN can be deduced from the corresponding human fibronectin precursor sequence which is available on the SwissProt database under accession number P02751. The sequence of the mouse A-FN can be deduced from the corresponding mouse fibronectin precursor sequence which is available on the SwissProt database under accession number P11276.

The A-FN may be the human ED-A isoform of fibronectin. The ED-A may be the Extra Domain-A of human fibronectin.

ED-A is a 90 amino acid sequence which is inserted into fibronectin (FN) by alternative splicing and is located between domain 11 and 12 of FN (Borsi et al., 1987, J. Cell Biol., 104, 595-600). ED-A is mainly absent in the plasma form of FN but is abundant during embryogenesis, tissue remodelling, fibrosis, cardiac transplantation and solid tumour growth.

Tenascin-C

Tenascin-C is a large hexameric glycoprotein of the extracellular matrix which modulates cellular adhesion. It is involved in processes such as cell proliferation and cell migration and is associated with changes in tissue architecture as occurring during morphogenesis and embryogenesis as well as under tumourigenesis or angiogenesis. A schematic representation of the small (A) and large (B) tenascin-C isoform is shown in FIG. 1.

A strong over-expression of the large isoform of tenascin-C has been reported for a number of tumours, and monoclonal antibodies specific for domains A1 and D, respectively, have been extensively characterised in the clinic (Riva et al., 1992; Riva et al., 1995; Paganelli et al., 1994; Reardon et al., 2002; Bigner et al., 1998).

Various further aspects and embodiments of the present invention will be apparent to those skilled in the art in view of the present disclosure. All documents and database entries mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example. All documents and database entries mentioned in this specification are incorporated herein by reference in their entirety.

EXPERIMENTS

Figure 1:
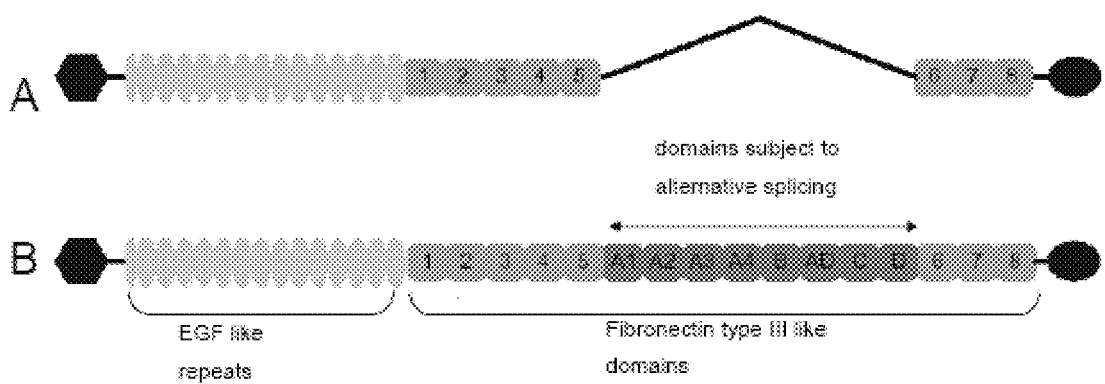
FIG. 1 shows a schematic representation of the small (A) and large (B) tenascin-C isoform. Several fibronectin type III like domains are subject to alternative splicing, either being included (B) or omitted (A) in the molecule. The amino acid sequence and encoding nucleotide sequence of tenascin C are publically available under sequence database references NP_002151.1 GI:4504549 and NM_002160.1 GI:4504548, respectively.

The below experiments show that specific antigens, such as tenascin-C and the ED-A isoform of fibronectin, are expressed in bone marrow neovasculature, e.g. the neovasculature present in the bone marrow of leukaemia patients, in particular those with AML.

Materials and Methods
Antibodies

4A1-F16-SIP is a human monoclonal mini-immunoglobulin specific to the A1 domain of tenascin-C. The sequence of the 4A1-F16-SIP antibody is shown in SEQ ID NO:25.

F8-SIP (V5L/K18R) is a human monoclonal mini-immunoglobulin specific to the alternatively spliced EDA domain of fibronectin. The sequence of the F8-SIP (V5L/K18R) antibody is shown in SEQ ID NO:26.

Bone Marrow Biopsies

Immunohistochemistry and immunofluorescence analysis were performed on freshly frozen bone marrow biopsies of patients with acute myeloid leukaemia.

Immunohistochemistry

For immunohistochemistry, biotinylated antibodies were used in small immunoprotein format (SIP) under identical conditions (2 μg/ml). Aliquots were prepared from a single batch of antibodies, frozen and used only once to ensure reproducibility of immunohistochemical stainings. Frozen tissue samples were stored at −80° C. Sections of 10 μm thickness were fixed in chilled acetone, rehydrated in TBS buffer (50 mM Tris, 100 mM NaCl, 0.001% Aprotinin, pH 7.4) and blocked with 20% fetal calf serum in TBS. The antibodies were added onto the sections in a final concentration of 2 μg/mL in 3% bovine serum albumin (BSA)/TBS solution and incubated for one hour. After washing in TBS, bound antibodies were detected with streptavidin-biotinylated alkaline phosphatase complex (Biospa, Milan, Italy) in TBS 3% BSA+2 mM $MgCl_2$. The Fast Red substrate (Sigma) was used for detection of phosphatase activity. Sections were counterstained with Gill's hematoxylin No. 2 (Sigma) and mounted with Glycergel mounting medium (Dako, Glostrup, Denmark).

Multicolour Immunofluorescence Studies

Biotinylated antibodies were used in small immunoprotein format (SIP) under identical conditions (2 μg/ml). Aliquots were prepared from a single batch of antibodies, frozen and used only once to ensure reproducibility of immunohistochemical stainings.

Sections of 10 μm thickness were fixed in chilled acetone and blocked with 20% fetal calf serum in PBS. Biotinylated F8-SIP (V5L/K18R) and 4A1-F16-SIP were added onto the sections in a final concentration of 2 μg/mL in 3% bovine serum albumin (BSA)/PBS solution and incubated for one hour. Mouse anti-human vWF (von Willebrandt factor) was used to outline endothelial cells. After washing in PBS, bound primary antibodies were detected with Streptavidin-Alexa Fluor 488 and anti-mouse IgG Alexa Fluor 594 (Invitrogen) were used as secondary antibodies. Nuclei were counterstained with DAPI and images were captured on an Axioskop 2 Mot plus microscope equipped with an Axio-Cam MRc camera (Zeiss). Human Leukaemia Mouse Model The mouse model for human leukaemia used here was previously described in Potter et al. (1984). Specifically, nude mice were xenografted with cells from the HL-60 leukaemia cell line and, after development of HL-60 tumours (granulocytic sarcomas), samples were obtained both from said tumours and from the bone marrow of the mice.

Immunohistochemistry studies were then performed as described under "immunohistochemistry" above.

Results

Figure 2:
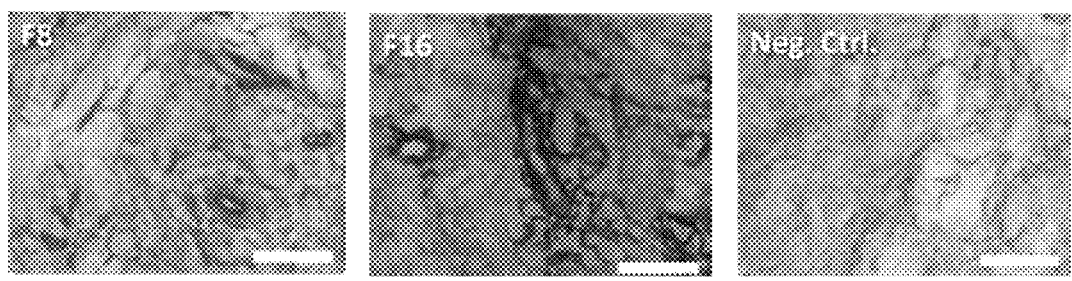
FIGS. 2 A and B show the results of immunohistochemical analyses of bone marrow biopsies from a patient with AML, stained with either the F8-SIP (V5L/K18R) (F8) or 4A1-F16-SIP (F16) antibody, as indicated. The negative control in each case is a bone marrow biopsy from the same patient stained with streptavidin-biotinylated alkaline phosphatase complex only. 4A1-F16-SIP strongly stained the blood vessels present in the bone marrow biopsy. Staining with F8-SIP (V5L/K18R) was also visible, although the level of staining was weaker than that observed with 4A1-F16-SIP. No staining was observed in the negative control. The size of the scale bar shown in FIG. 1A is 100 μm.
Figure 2:
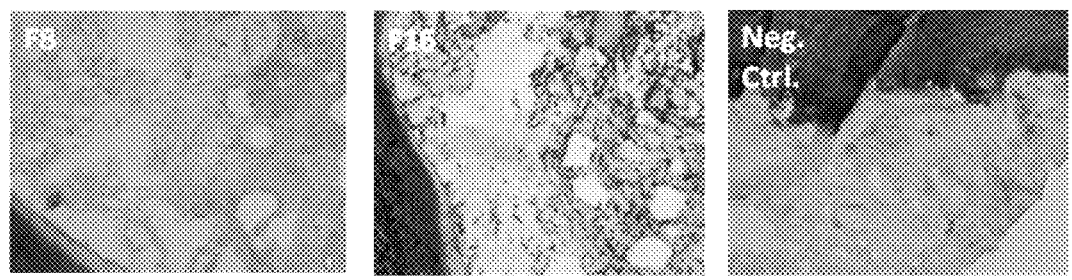

Immunohistochemistry analysis showed that antibody 4A1-F16-SIP was capable of staining the vast majority of blood vessels in the bone marrow of AML patients. Antibody F8-SIP (V5L/K18R) also stained a large proportion of these blood vessels but fewer than observed with the 4A1-F16-SIP antibody. These results are shown in FIGS. 2 A and B.

Figure 3:
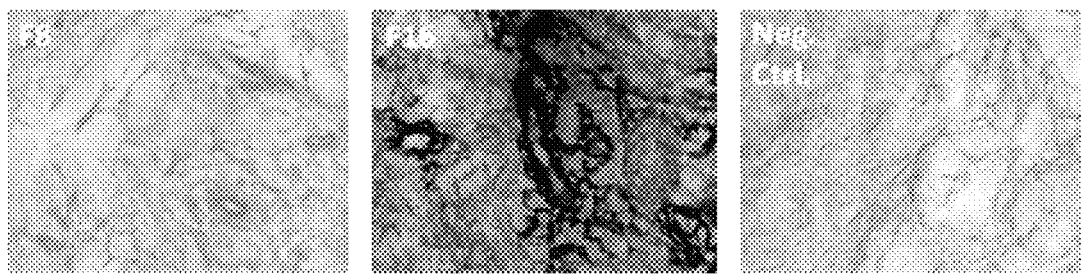
FIGS. 3 A and B show immunohistochemical analyses of bone marrow biopsies from two patients with extramedullar AML, stained with either the F8-SIP (V5L/K18R) (F8) or 4A1-F16-SIP (F16) antibody, as indicated. The negative control in each case is a bone marrow biopsy from the same patient stained with streptavidin-biotinylated alkaline phosphatase complex only. 4A1-F16-SIP strongly stained the blood vessels present in the bone marrow biopsies. Staining with F8-SIP (V5L/K18R) was also visible and was either similar or slightly weaker than the level of staining observed with 4A1-F16-SIP. No staining was observed in the negative control.
Figure 3:
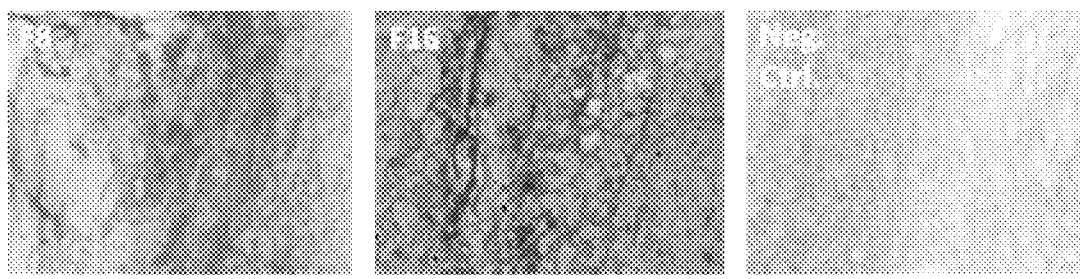

Similar results were obtained when bone marrow biopsies from two patients with extramedullary AML were subjected to immunohistochemistry analysis. Antibody 4A1-F16-SIP strongly stained the blood vessels present in the bone marrow biopsies in both cases. The level of staining observed with antibody F8-SIP (V5L/K18R) was similar to that observed using antibody 4A1-F16-SIP in one biopsy (FIG. 3B) but weaker in the other (FIG. 3A).

The differences in the level of staining observed with antibodies F8-SIP (V5L/K18R) and 4A1-F16-SIP may be due to differences in the level of expression of domain A1 of tenascin-C relative to the ED-A isoform of fibronectin in the bone marrow blood vessels of AML patients.

Multicolour immunofluorescence studies of areas of bone marrow from AML patients with high blast densities further showed an excellent co-localization of antibody 4A1-F16-SIP with antibodies specific for von Willebrand Factor (vWF).

Figure 4:
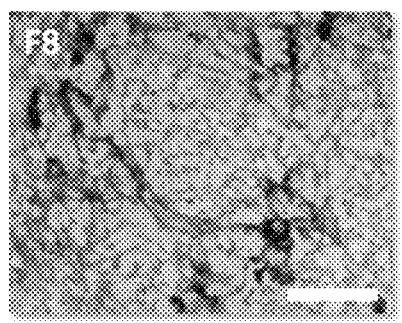
FIG. 4 A shows immunohistochemical analyses of HL-60 tumours obtained from a human leukaemia mouse model stained with either the F8-SIP (V5L/K18R) (F8) or 4A1-F16-SIP (F16) antibody, as indicated. B shows immunohistochemical analyses of bone marrow biopsies obtained from the same mice as in A and also stained with either the F8-SIP (V5L/K18R) (F8) or 4A1-F16-SIP (F16) antibody, as indicated. Both antibodies strongly stained the vessels of the HL-60 tumour sections, while no staining was visible with either antibody in the sections of healthy bone marrow. The size of the scale bar shown in FIGS. 4 A and B is 100 μm.
Figure 4:
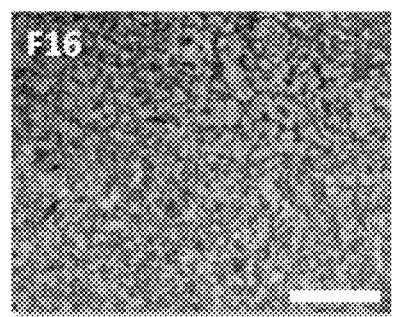
Figure 4:
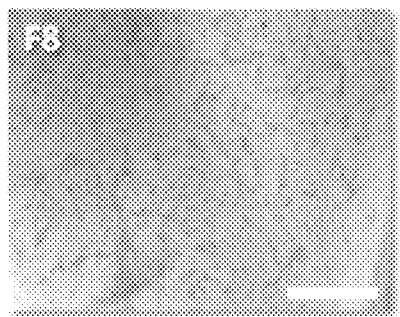
Figure 4:
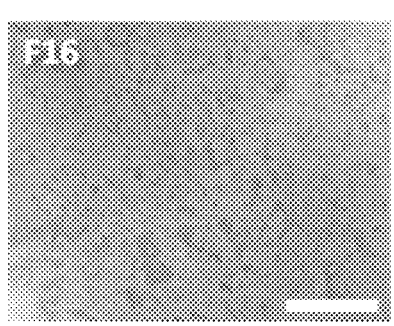

Antibodies 4A1-F16 SIP and the F8-SIP (V5L/K18R) also stained sections HL-60 tumours obtained from a mouse model of human leukaemia. Specifically, both of antibodies strongly stained the vessels present in the HL-60 tumour (granulocytic sarcoma) sections, while no staining was visible in the sections of healthy bone marrow obtained from the same mice (FIG. 4).

These results show for the first time that antigens exist which are differentially expressed in the bone marrow neovasculature, in particular the bone marrow neovasculature of leukaemia patients, compared to normal tissues. The results also show that the same antigens are also differentially expressed in the neovasculature of tumours formed by leukaemic cells, such as granulocytic sarcomas, compared to normal tissues. These antigens therefore represent attractive targets for the development of selective and efficient pharmacodelivery strategies in the treatment of diseases characterised by bone marrow neovasculature, such as leukaemia. In particular, as targets present in vasculature are often more easily accessible from the bloodstream to systemically administered agents, overcoming the problem of access and allowing an efficient delivery of the compound to the site of disease.

For example, the antigens expressed in bone marrow neovasculature, such as the bone marrow neovasculature of leukaemia patients, can be targeted using antibodies capable of binding to said antigens. By conjugating bioactive agents to said antibodies, the bioactive agents can be delivered directly to the bone marrow neovasculature. Selective targeting of the bioactive agent to the site of disease will ultimately result in an increased local concentration at its site of action, thus reducing or eliminating the exposure of normal tissues to any toxic effects of the bioactive agent used. Such a targeted delivery can improve the therapeutic index of the delivered bioactive agent by providing a higher efficacy with minimized side effects. In addition, the favourable toxicity profile of site-specific therapeutics may open new avenues in the therapy of diseases characterized by bone marrow neovasculature, such as leukaemia, by allowing the systemic administration of highly potent and promising agents, which are currently either given at suboptimal doses or whose clinical application has to date been impeded by unacceptable toxicities when applied in an unmodified form.

Sequences—4A1-F16 Antibody

```
                                                        SEQ ID NO: 1
4A1-F16 VH domain nucleotide sequence.
GAG GTG CAG CTG TTG GAG TCT GGG GGA GGC TTG GTA CAG CCT GGG GGG

TCC CTG AGA CTC TCC TGT GCA GCC TCT GGA TTC ACC TTT AGC CGG TAT GGT

ATG AGC TGG GTC CGC CAG GCT CCA GGG AAG GGG CTG GAG TGG GTC TCA

GCT ATT AGT GGT AGT GGT GGT AGC ACA TAC TAC GCA GAC TCC GTG AAG GGC

CGG TTC ACC ATC TCC AGA GAC AAT TCC AAG AAC ACG CTG TAT CTG CAA ATG

AAC AGC CTG AGA GCC GAG GAC ACG GCC GTA TAT TAC TGT GCG AAA GCG CAT

AAT GCT TTT GAC TAC TGG GGC CAG GGA ACC CTG GTC ACC GTG TCG AGA

SEQ ID NO: 2
4A1-F16 VH domain amino acid sequence
EVQLLESGGG LVQPGGSLRL SCAASGFTFS RYGMSWVRQA PGKGLEWVSA

ISGSGGSTYY ADSVKGRFTI SRDNSKNTLY LQMNSLRAED TAVYYCAKAH

NAFDYWGQGT LVTVSR

SEQ ID NO: 3
4A1-F16 VL domain nucleotide sequence
TCT TCT GAG CTG ACT CAG GAC CCT GCT GTG TCT GTG GCC TTG GGA CAG ACA

GTC AGG ATC ACA TGC CAA GGA GAC AGC CTC AGA AGC TAT TAT GCA AGC TGG

TAC CAG CAG AAG CCA GGA CAG GCC CCT GTA CTT GTC ATC TAT GGT AAA AAC

AAC CGG CCC TCA GGG ATC CCA GAC CGA TTC TCT GGC TCC AGC TCA GGA AAC

ACA GCT TCC TTG ACC ATC ACT GGG GCT CAG GCG GAA GAT GAG GCT GAC TAT

TAC TGT AAC TCC TCT GTT TAT ACT ATG CCG CCC GTG GTA TTC GGC GGA GGG

ACC AAG CTG ACC GTC CTA

SEQ ID NO: 4
4A1-F16 VL domain amino acid sequence
SSELTQDPAVSVALGQTVRITCQGDSLRSYYASWYQQKPGQAPVLVIYGKNNRPSGIPDR

FSGSSSGNTASLTITGAQAEDEADYYCNSSVYTMPPVVFGGGTKLTVL

SEQ ID NO: 5
4A1-F16 VH CDR1 amino acid sequence
RYGMS

SEQ ID NO: 6
4A1-F16 VH CDR2 amino acid sequence
AISGSGGSTYYADSVKG

SEQ ID NO: 7
4A1-F16 VH CDR3 amino acid sequence
AHNAFDY
```

-continued

SEQ ID NO: 8
4A1-F16 VL CDR1 amino acid sequence
QGDSLRSYYAS

SEQ ID NO: 9
4A1-F16 VL CDR2 amino acid sequence
GKNNRPS

SEQ ID NO: 10
4A1-F16 VL CDR3 amino acid sequence
NSSVYTMPPVV

SEQ ID NO: 11
4A1-F16 VH and VL domain peptide linker amino acid sequence
GGGSGGGSGG Sequences—F8 (V5L/K18R) Antibody SEQ ID NO: 12
F8 (V5L) VH domain nucleotide sequence
GAGGTGCAGCTGTTGGAGTCTGGGGGAGGCTTGGTACAGCCTGGGGGGTCCCTGAGA

CTCTCCTGTGCAGCCTCTGGATTCACCTTTAGCCTGTTTACGATGAGCTGGGTCCGCCA

GGCTCCAGGGAAGGGGCTGGAGTGGGTCTCAGCTATTAGTGGTAGTGGTGGTAGCAC

ATACTACGCAGACTCCGTGAAGGGCCGGTTCACCATCTCCAGAGACAATTCCAAGAAC

ACGCTGTATCTGCAAATGAACAGCCTGAGAGCCGAGGACACGGC

SEQ ID NO: 13
F8 (V5L) VH domain amino acid sequence
EVQLLESGGGLVQPGGSLRLSCAASGFTFSLFTMSWVRQAPGKGLEWVSAISGSGGSTYY

ADSVKGRFTISRDNSKNTLYLQMNSLRAEDTAVYYCAKSTHLYLFDYWGQGTLVTVSS

SEQ ID NO: 14
F8 (K18R) VL domain nucleotide sequence
GAAATTGTGTTGACGCAGTCTCCAGGCACCCTGTCTTTGTCTCCAGGGGAAAGAGCCA

CCCTCTCCTGCAGGGCCAGTCAGAGTGTTAGCATGCCGTTTTTAGCCTGGTACCAGCA

GAAACCTGGCCAGGCTCCCAGGCTCCTCATCTATGGTGCATCCAGCAGGGCCACTGG

CATCCCAGACAGGTTCAGTGGCAGTGGGTCTGGGACAGACTTCACTCTCACCATCAGC

AGACTGGAGCCTGAAGATTTTGCAGTGTATTACTGTCAGCAGATGCGTGGTCGGCCGC

CGACGTTCGGCCAAGGGACCAAGGTGGAAATCAAA

SEQ ID NO: 15
F8 (K18R) VL domain amino acid sequence
EIVLTQSPGTLSLSPGERATLSCRASQSVSMPFLAWYQQKPGQAPRLLIYGASSRATGIPD

RFSGSGSGTDFTLTISRLEPEDFAVYYCQQMRGRPPTFGQGTKVEIK

SEQ ID NO: 16
F8 (V5L) VH CDR1 amino acid sequence
LFT

SEQ ID NO: 17
F8 (V5L) VH CDR2 amino acid sequence
SGSGGS

SEQ ID NO: 18
F8 (V5L) VH CDR3 amino acid sequence
STHLYL

SEQ ID NO: 19
F8 (K18R) VL CDR1 amino acid sequence
MPF

SEQ ID NO: 20
F8 (K18R) VL CDR2 amino acid sequence
GASSRAT

SEQ ID NO: 21
F8 (K18R) VL CDR3 amino acid sequence
MRGRPP

-continued

SEQ ID NO: 22
F8 (V5L/K18R) VH and VL domain peptide linker amino acid sequence
GGGGSGGGSGGGG SEQ ID NO: 23
4A1-F16-SIP and F8-SIP (V5L/K18R) VL and CH4 domain peptide linker
amino acid sequence
SG SEQ ID NO: 24
amino acid sequence of CH4 dimerization domain of 4A1-F16-SIP and F8-
SIP (V5L/K18R)
GSGGPRAAPEVYAFATPEWPGSRDKRTLACLIQNFMPEDISVQWLHNEVQLPDARHSTTQ

PRKTKGSGFFVFSRLEVTRAEWEQKDEFICRAVHEAASPSQTVQRAVSVNPESSRRGGC

SEQ ID NO: 25
4A1-F16-SIP amino acid sequence
EVQLLESGGGLVQPGGSLRLSCAASGFTFSRYGMSWVRQAPGKGLEWVSAISGSGGSTY

YADSVKGRFTISRDNSKNTLYLQMNSLRAEDTAVYYCAKAHNAFDYWGQGTLVTVSRGGG

SGGGSGGGSSELTQDPAVSVALGQTVRITCQGDSLRSYYASWYQQKPGQAPVLVIYGKNNR

PSGIPDRFSGSSSGNTASLTITGAQAEDEADYYCNSSVYTMPPVVFGGGTKLTVLSGGSGG

PRAAPEVYAFATPEWPGSRDKRTLACLIQNFMPEDISVQWLHNEVQLPDARHSTTQPRKT

KGSGFFVFSRLEVTRAEWEQKDEFICRAVHEAASPSQTVQRAVSVNPESSRRGGC

SEQ ID NO: 26
F8-SIP (V5L/K18R) amino acid sequence
EVQLLESGGGLVQPGGSLRLSCAASGFTFSLFTMSWVRQAPGKGLEWVSAISGSGGSTYY

ADSVKGRFTISRDNSKNTLYLQMNSLRAEDTAVYYCAKSTHLYLFDYWGQGTLVTVSSGG

GGSGGGSGGGGGEIVLTQSPGTLSLSPGERATLSCRASQSVSMPFLAVVYQQKPGQAPRL

LIYGASSRATGIPDRFSGSGSGTDFTLTISRLEPEDFAVYYCQQMRGRPPTFGQGTKVEIKS

GGSGGPRAAPEVYAFATPEWPGSRDKRTLACLIQNFMPEDISVQWLHNEVQLPDARHSTT

QPRKTKGSGFFVFSRLEVTRAEWEQKDEFICRAVHEAASPSQTVQRAVSVNPESSRRGGC

Sequences—Interleukin 2

SEQ ID NO: 27
hIL2 precursor sequence (mature hIL2: residues
7-150)
MYRMQLLSCI ALSLALVTNS APTSSSTKKT QLQLEHLLLD

LQMILNGINN YKNPKLTRML TFKFYMPKKA TELKHLQCLE

EELKPLEEVL NLAQSKNFHL RPRDLISNIN VIVLELKGSE

TTFMCEYADE TATIVEFLNR WITFCQSIIS TLT

SEQ ID NO: 28
IL-2 linker sequence
GGGGSGGGGSGGGG

SEQ ID NO: 29
IL-2 linker sequence
GGGGSGGGGSGGGGS

SEQ ID NO: 30
IL-2 linker sequence
SSSSGSSSSGSSSSG

SEQ ID NO: 31
IL-2 linker sequence
GSGSAGSGSAGSGSA

SEQ ID NO: 32
IL-2 linker sequence
GGSGGGGSGGGGSGG

REFERENCES

Amit et al. (1986), Science, 233:747-753.
Barnett, C. J., et al., J Med Chem, 1978. 21(1): p. 88-96.
Berndorff, D., et al., J Nucl Med, 2006. 47(10): p. 1707-16.
Birchler, M., et al., Nat Biotechnol, 1999. 17(10): p. 984-8.
Borsi et al., J. Cell. Biol., 1987. 104, 595-600.
Borsi, L., et al., Int J Cancer, 2002. 102(1): p. 75-85.
Brack et al. Clin Cancer Res, 2006. 12(10): 3200-3208.
Carnemolla, B., et al., Blood, 2002. 99(5): p. 1659-65.
Carter, P. J. and P. D. Senter, Cancer J, 2008. 14(3): p. 154-69.
Caton et al. (1990), J. Immunol., 144:1965-1968.
Chothia et al. (1987), J. Mol. Biol., 196:901-917.
Chothia et al. (1989), Nature, 342:877-883.
de Arruda, M., et al., Cancer Res, 1995. 55(14): p. 3085-92.
Fabbrini, M., et al., Int J Cancer, 2006. 118(7): p. 1805-13.
Feldman et al, 2003, Leukemia, 17, 314-318.
Feldman et al, 2005, J Clin Oncol, 23, 4110-4116.
Haan et al. (2004), BioCentury, 12(5): A1-A6.
Jin et al., Cell Stem cell 2009 Jul. 2; 5(1):31-42.
Kabat et al. (1987) Sequences of Proteins of Immunological Interest. 4th Edition. US Department of Health and Human Services.
Kabat et al. (1991a), Sequences of Proteins of Immunological Interest, 5th Edition. US Department of Health and Human Services, Public Service, NIH, Washington.
Kabat et al. (1991b), J. Immunol., 147:1709-1719.
Kobayashi et al., Int. J. Hematol, 2009, 89, 460-469.

Koide et al. (1998), Journal of Molecular Biology, 284: 1141-1151.
Leamon, C. P., et al., Int J Cancer, 2007. 121(7): p. 1585-92.
Marlind, et al., Clin Cancer Res, 2008. 14(20): p. 6515-24.
Martin, A. C. R. Accessing the Kabat Antibody Sequence Database by Computer PROTEINS: Structure, Function and Genetics, 25 (1996), 130-133
Menrad, A. and H. D. Menssen, 2005. 9(3): p. 491-500.
Neri, D., G. Fossati, and M. Zanda, ChemMedChem, 2006. 1(2): p. 175-80.
Nilsson, F., et al., Cancer Res, 2001. 61(2): p. 711-6.
Nygren et al. (1997), Current Opinion in Structural Biology, 7: 463-469.
Padro, T., et al., Blood, 2000. 95(8): p. 2637-44.
Paganelli G et al., Eur J Nucl Med 21:314-321 1994
Patterson, A. W. et al., Chemistry, 2007. 13(34): p. 9534-41.
Potter et al., Am J. Pathol., 1984, 114, 360-366
Ray, A., et al., Cancer Res, 2007. 67(8): p. 3767-76.
Reardon D A et al. J Clin Oncol 20:1389-1397 2002
Reddy, J. A., et al., Cancer Res, 2007. 67(9): p. 4434-42.
Riva P et al. Int J Cancer; 51:7-13 1992
Riva P et al. Cancer Res 55:5952s-5956s 1995
Rybak, J. N., et al., Nat Methods, 2005. 2(4): p. 291-8.
Sani, M., et al., Angew Chem Int Ed Engl, 2007. 46(19): p. 3526-9.
Sharon et al. (1990a), PNAS, 87:4814-4817.
Sharon et al. (1990b), J. Immunol., 144:4863-4869.
Schliemann et al., Blood, 2009. 113(10): p. 2275-83.
Segal et al. (1974), PNAS, 71:4298-4302.
Villa A et al. Int. J. Cancer. 2008 Jun. 1; 122(11):2405-13.
Wess In: BioCentury, The Bernstein Report on BioBusiness, 12(42), A1-A7, 2004

The invention claimed is:

1. A method of treating acute myeloid leukemia in an individual in need thereof, said method consisting essentially of administering to said individual a therapeutically effective amount of an antibody that binds an antigen which is differentially expressed in the bone marrow neovasculature in acute myeloid leukemia patients, said antigen being the Extra Domain-A (ED-A) isoform of fibronectin and said antibody having an antigen binding site comprising a VH domain and a VL domain, said VH domain comprising a VH CDR1 of SEQ ID NO:16, a VH CDR2 of SEQ ID NO:17 and a VH CDR3 of SEQ ID NO:18, and said VL domain comprising a VL CDR1 of SEQ ID NO:19, a VL CDR2 of SEQ ID NO:20 and a VL CDR3 of SEQ ID NO:21.

2. The method of claim 1, wherein the antibody is conjugated to a bioactive molecule, said bioactive molecule being selected from the group consisting of a cytokine, cytotoxic agent, photosensitizer and a therapeutic radioisotope.

3. The method of claim 2, wherein the antibody is conjugated to the bioactive molecule via a cleavable linker.

4. The method of claim 1 wherein the VH domain is the F8 V5L VH domain of SEQ ID NO:13and the VL domain is the F8 K18R VL domain of SEQ ID NO:15.

5. The method of claim 1, wherein the antibody is a small immunoprotein (SIP), scFv, or whole IgG molecule.

6. The method of claim 2, wherein the VH domain is the F8 V5L VH domain of SEQ ID NO:13, and the VL domain is the F8 K18R VL domain of SEQ ID NO:15.

7. The method of claim 3, wherein the VH domain is the F8 V5L VH domain of SEQ ID NO:13, and the VL domain is the F8 K18R VL domain of SEQ ID NO:15.

* * * * *

UNITED STATES PATENT AND TRADEMARK OFFICE
CERTIFICATE OF CORRECTION

PATENT NO. : 9,446,124 B2  
APPLICATION NO. : 14/219145  
DATED : September 20, 2016  
INVENTOR(S) : Manuela Kaspar, Christoph Schliemann and Dario Neri Page 1 of 1

It is certified that error appears in the above-identified patent and that said Letters Patent is hereby corrected as shown below:

On the Title Page

Item (73) Assignee:
Please delete "Philochem AG, Zurich (CH)" and insert therefor --Philogen S.P.A., Siena (IT)--.

Signed and Sealed this
Thirty-first Day of August, 2021

Drew Hirshfeld
*Performing the Functions and Duties of the*
*Under Secretary of Commerce for Intellectual Property and*
*Director of the United States Patent and Trademark Office*